United States Patent [19]
Roller et al.

[11] Patent Number: 5,980,814
[45] Date of Patent: *Nov. 9, 1999

[54] METHOD FOR MAKING AN APERTURED FILM COATED WITH A SURFACE-ACTIVE AGENT

[75] Inventors: Judith E. Roller, North Brunswick; Thomas Patrick Luchino, Freehold; David A. Burwell, Hopewell, all of N.J.; Sunita Pargass, Wynnewood, Pa.

[73] Assignee: McNeil-PPC, Inc., Skillman, N.J.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/522,600

[22] Filed: Sep. 1, 1995

[51] Int. Cl.$^6$ ............................ B29C 59/00; B29C 67/20; B05D 1/02

[52] U.S. Cl. ............................ 264/455; 264/504; 264/134; 264/135; 264/136; 264/129; 264/130; 427/314; 427/316; 427/424; 427/428; 427/434.2

[58] Field of Search ...................................... 264/504, 423, 264/483, 134, 136, 455, 546, 156, 129, 135, 130; 427/314, 316, 424, 428, 434.2

[56] References Cited

U.S. PATENT DOCUMENTS

| | | |
|---|---|---|
| 3,262,808 | 7/1966 | Crooks et al. ............................ 264/455 |
| 3,391,070 | 7/1968 | Morgan .................... 264/455 |
| 3,632,269 | 1/1972 | Doviak et al. . |
| 3,880,966 | 4/1975 | Zimmerman et al. .................... 264/25 |
| 3,929,135 | 12/1975 | Thompson . |
| 4,077,410 | 3/1978 | Butterwoth et al. . |
| 4,324,246 | 4/1982 | Mullane et al. . |
| 4,351,784 | 9/1982 | Thomas et al. . |
| 4,381,326 | 4/1983 | Kelly . |
| 4,456,570 | 6/1984 | Thomas et al. . |
| 4,535,020 | 8/1985 | Thomas et al. . |
| 4,609,518 | 9/1986 | Curro et al. . |
| 4,690,679 | 9/1987 | Mattingly, III et al. . |
| 4,778,634 | 10/1988 | Douglas ........................ 264/22 |
| 4,839,216 | 6/1989 | Curro et al. . |
| 4,950,264 | 8/1990 | Osborn, III . |
| 5,009,653 | 4/1991 | Osborn, III . |
| 5,112,690 | 5/1992 | Cohen et al. ................... 428/411.1 |
| 5,342,334 | 8/1994 | Thompson . |
| 5,352,217 | 10/1994 | Curro . |
| 5,368,910 | 11/1994 | Langdon . |
| 5,368,926 | 11/1994 | Thompson et al. . |
| 5,376,439 | 12/1994 | Hodgson et al. . |
| 5,382,245 | 1/1995 | Thompson et al. . |
| 5,382,703 | 1/1995 | Nohr et al. . |
| 5,383,870 | 1/1995 | Takai et al. . |
| 5,387,290 | 2/1995 | Yamamoto et al. . |
| 5,520,875 | 5/1996 | Wnuk et al. ............................ 264/504 |
| 5,567,376 | 10/1996 | Turi et al. ............................ 264/455 |
| 5,770,144 | 6/1998 | James et al. ............................ 264/504 |

FOREIGN PATENT DOCUMENTS

| | | |
|---|---|---|
| 0215684 | 3/1987 | European Pat. Off. ............... 264/546 |
| 0 432 882 A2 | 6/1991 | European Pat. Off. . |
| 0 598 204 A1 | 5/1994 | European Pat. Off. . |
| 0 626 158 A1 | 11/1994 | European Pat. Off. . |
| 0 626 159 A1 | 11/1994 | European Pat. Off. . |
| 0 304 617 B1 | 1/1995 | European Pat. Off. . |
| 0 640 328 A1 | 3/1995 | European Pat. Off. . |
| 6007851 | 2/1981 | Japan ..................... 264/483 |
| 3-286762 | 12/1991 | Japan . |
| WO 93/15701 | 2/1992 | WIPO . |
| WO 94/18926 | 2/1994 | WIPO . |
| WO 94/22408 | 3/1994 | WIPO . |
| WO 92/18078 | 4/1994 | WIPO . |
| WO 94/28846 | 6/1994 | WIPO . |
| WO 95/00093 | 6/1994 | WIPO . |

Primary Examiner—Jan H. Silbaugh
Assistant Examiner—Robin S. Gray

[57] ABSTRACT

A method for making an apertured film for use as a topsheet in absorbent products wherein the film is corona treated on one side, and has received a surfactant application that is distributed to both the corona treated and non-corona treated sides of the film. A method for application of surfactant includes applying the surfactant to one side of the film and rolling the film into a roll while the surfactant is still wet in order to apply surfactant to both sides of the film.

27 Claims, 18 Drawing Sheets

Fig. 14
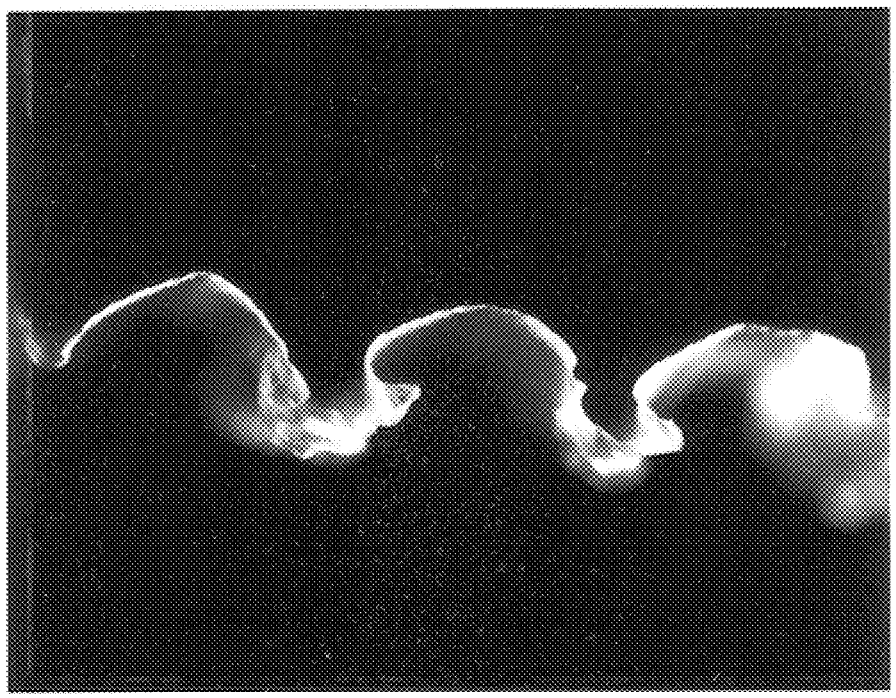
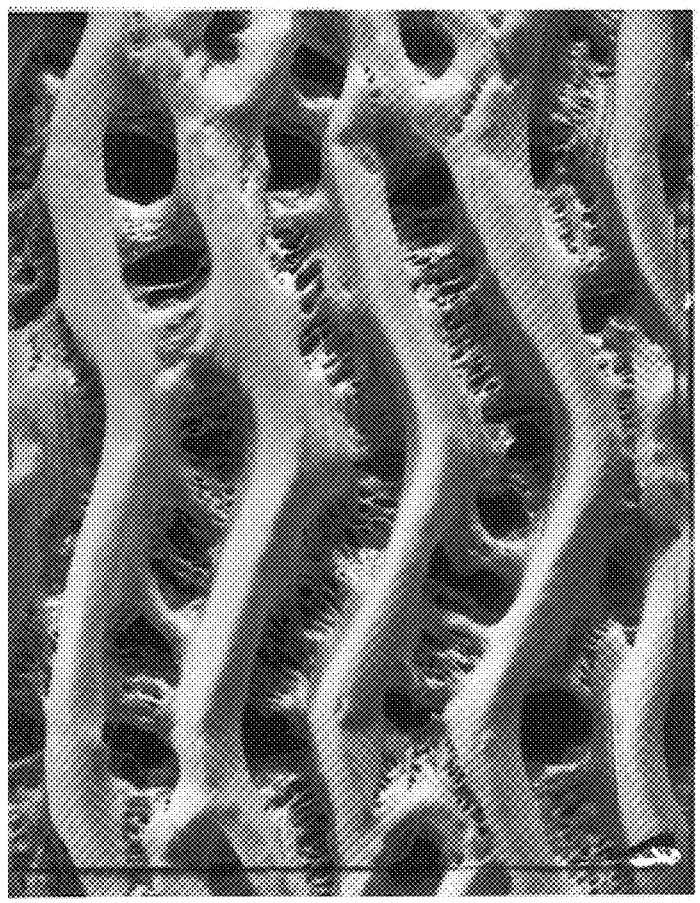
Fig. 15

METHOD FOR MAKING AN APERTURED FILM COATED WITH A SURFACE-ACTIVE AGENT

FIELD OF THE INVENTION

This invention relates to apertured films having primary utility as a cover member for an absorbent article, and to methods and apparatus for forming such apertured films.

BACKGROUND OF THE INVENTION

For many years it has been common to use nonwoven fabrics as a cover member, or facing layer, for products that are adapted to receive body discharges, such as disposable diapers, sanitary napkins, adult incontinent devices, wound dressings and the like. Such fabrics have typically been formed by air-laying, carding, spun bonding and the like, and it is known to post-treat such fabrics to provide strength and integrity, as by the application of binders or fiber entanglement, either mechanically or by the application of fluid forces. Since such fabrics are often formed of hydrophobic material, it is also known to post-treat such fabrics with surface active agents to promote the passage of body discharges through the fabric. Such fabrics have, or are perceived to have, desirable characteristics such as breathability, drapeability, softness, and pleasant hand and tactile impression.

One of the drawbacks associated with facing layers formed of a nonwoven fabric is that liquid, such as urine, menses, wound exudate, and the like, that passes through the facing layer and into the absorbent core has a tendency to strike back through the facing layer, particularly under pressure and when the liquid in the absorbent core approaches the volumetric storage capacity of the core. For this reason, and other reasons, it has been known in the past to utilize apertured plastic films as the facing layer in absorbent articles.

The following list includes disclosures of such apertured films in issued U.S. and foreign patents and published patent applications.

U.S. Pat. No. 3,632,269—Doviak et al.
U.S. Pat. No. 3,929,135—Thompson et al.
U.S. Pat. No. 4,324,276—Mullane
U.S. Pat. No. 4,351,784—Thomas et al.
U.S. Pat. No. 4,381,326—Kelly
U.S. Pat. No. 4,456,570—Thomas et al.
U.S. Pat. No. 4,535,020—Thomas et al.
U.S. Pat. No. 4,690,679—Mattingly et al.
U.S. Pat. No. 4,839,216—Curro et al.
U.S. Pat. No. 4,950,264—Osborn
U.S. Pat. No. 5,009,653—Osborn
U.S. Pat. No. 5,112,690—Cohen et al.
U.S. Pat. No. 5,342,334—Thompson et al.
U.S. Pat. No. 5,352,217—Curro
U.S. Pat. No. 5,368,910—Langdon
U.S. Pat. No. 5,368,926—Thompson et al.
U.S. Pat. No. 5,376,439—Hodgson et al.
U.S. Pat. No. 5,382,245—Thompson et al.
U.S. Pat. No. 5,382,703—Nohr et al.
U.S. Pat. No. 5,383,870—Takai et al.
U.S. Pat. No. 5,387,209—Yamamoto et al.
EP 0 304 617—Suda et al.
EP 0 432 882 A2—Shipley
EP 0 598 204 A1—Garavaglia et al.
EP 0 626 158 A1—Coles et al.
EP 0 626 159 A1—Taki et al.
EP 0 640 328—Tanaka et al.
JP 3-286762 A—Yamamoto et al.
WO 92/18078 A1—Colbert
WO 93/15701 A1—Turi et al.
WO 94/18926 A1—Perry
WO 94/22408 A1—Langdon
WO 94/28846 A1—Steiger et al.
WO 95/00093 A2—Osborn et al.

While certain of such apertured films have functioned reasonably well for their intended purposes, the vast majority of such films have actual and perceived major deficiencies. For example, even though such apertured films may permit fluid to readily pass therethrough, and may minimize strike-back of such fluid, such apertured films nevertheless tend to have the appearance, feel and hand of a film, rather than a fabric. Such film-like characteristics are considered as a negative by the consumer, and thus absorbent products with apertured films as a facing layer have not met with widespread consumer acceptance.

Major improvements for apertured film facing layers for absorbent products are disclosed in commonly assigned, copending U.S. patent application Ser. Nos. 08/417,404 and 08/417,408 to Turi et al. filed Apr. 5, 1995 as a continuation and a division of Ser. No. 08/004,379, filed Jan. 14, 1993 as a continuation of Ser. No. 07/744,744, filed Aug. 14, 1991 (corresponding to publication WO 93/15701 A1 on the above list). In the above-mentioned Turi et al. applications, an apertured film, and methods and apparatus for forming the film, are disclosed which impart to the film physical characteristics like those of nonwoven fabrics. This is accomplished by supporting a film formed of stretchable thermoplastic polymeric material on localized support regions of a backing member, and directing a fluid in the form of high pressure, small diameter columnar jets against the upper surface of the film, so that unsupported portions of the film are directed downwardly between the support regions to cause the formation of micro-holes and fiber-like elements (fibrils) thereabout to impart to the apertured film physical characteristics of appearance, softness, feel and hand, like those of a nonwoven fabric. While such apertured films are a marked improvement over prior art apertured films, it is desired to provide further improvements in such apertured films, as by improving the ability of such films to pass viscous fluids, such as menses, and as by improving the ability of such films to wick or transport liquid through the thickness of the film (in the z-direction), and to then wick liquid away (in the x and y direction, particularly on the underside of the film, that is, the side of the film facing the absorbent core) from an initially wetted zone so as to promote more efficient utilization of the absorbent capacity of the entire absorbent core.

For use of apertured films as topsheets for sanitary napkins, clean-dry properties are very much desired. This means that the sanitary napkin should appear clean and dry to the user even after it has accepted a flow of menstrual fluid. There are many factors affecting the clean-dry properties of a sanitary napkin, including the aperture characteristics and open area of the napkin cover material. There is a trade-off in the effects of the film aperture size and open area on clean-dry properties. On the one hand, large apertures allow the fluid to be more rapidly transmitted to the absorbent core. On the other hand, apertures that are too large permit the fluid to be transported back through the topsheet from the absorbent core (a phenomenon sometimes referred to as "strike back") and to contact the wearer. Furthermore, large open areas tend to allow the stain on the absorbent core of the napkin to be visible through the topsheet and give the wearer the perception that the product has not kept her clean. To exhibit both clean and dry properties, a topsheet must have a carefully balanced combination of aperture size and open area: large enough apertures to rapidly accept a flow of menstrual fluid and to allow it to pass through to the napkin's absorbent core, but small enough to mask the stain on the underlying absorbent core to give the wearer the perception of cleanliness.

SUMMARY OF THE INVENTION

In accordance with one aspect of the present invention, apertured films of the type disclosed in the above-mentioned Turi et al. patent applications are improved by providing such films with larger apertures and sufficient open area so that viscous fluids, such as menses, can flow readily through the film. These improved properties are imparted to the film by subjecting the film to fluid forces in the form of columnar streams or jets from at least two sets of orifices, the orifices of one set having a diameter greater than ten mils, and the fluid supplied to the orifices having a relatively low pressure less than about 500 psig, and the orifices of at least one other set having a diameter of less than or equal to ten mils and the fluid supplied thereto having a relatively high pressure greater than about 500 psig. The present invention can be practiced with selective variation of the sequence to which the film is subjected to fluid forces from the low and high pressure orifices, that is, first low pressure then high pressure, or first high pressure then low pressure, or other combinations or variations.

The apertures are, for the most part, irregular in shape and size. They are measured by various techniques that approximate the diameter, which may be expressed as equivalent hydraulic diameter (EHD) or equivalent circular diameter (ECD). The resulting apertured film has a combination of large sized apertures having average EHD's of from about 7 mils to about 30 mils, and small sized apertures having average EHD's from about 1 mil to about 7 mils. Such apertured films have an open area in the range of from about 3% to about 13%.

The improved apertured film of the present invention is preferably formed on a backing member like that shown in FIGS. 17–19 of the above-mentioned Turi et al. applications, which results in the film having a series of generally parallel ridges formed by generally vertically oriented side walls which define a series of generally parallel valleys. The film thus includes generally parallel alternating solid or closed portions of the film separated by apertured or open portions of the film, that contain the aforementioned combination of large and small sized apertures. Both size apertures are formed as a result of elongating and drawing the stretchable material between the localized support regions of the backing member as a result of the application of fluid pressure, and as the film elongates it undergoes thinning until it finally reaches the point of rupturing (i.e., splitting and fibrillating) to form the above-mentioned apertures.

As with apertured films disclosed in the Turi et al. applications, the apertures are surrounded by a network of fiber-like elements or micro-strips of drawn plastic material. Such drawn fiber-like elements (fibrils) cooperate with the apertures to provide the apertured film with physical characteristics similar to those of nonwoven fabrics. The fiber like elements have lengths varying from about 0.005 inch (0.013 cm) to about 0.05 inch (0.127 cm), widths ranging from about 0.001 inch (0.003 cm) to about 0.035 inch (0.089 cm), and thicknesses ranging from about 0.00025 inch (0.0006 cm) to about 0.002 inch (0.005 cm).

In accordance with the present invention, apertured films of the type disclosed in the above mentioned Turi et al. applications, and of the improved type disclosed and claimed in commonly assigned, concurrently filed, U.S. patent application Ser. No. 08/523,112 entitled "Method Of Forming Improved Apertured Films, Resultant Apertured Films, And Absorbent Products Incorporating Resultant Apertured Films" are modified so as to provide the film with improved fluid distribution properties in the regions of the film which have been subjected to stretching, by downward deflection of the film into the recessed regions of the support member, during formation of the film.

In accordance with the present invention, the apertured film is formed from a pre-embossed starting film having a female side with observable cupped recesses and a male side with observable protrusions, the male side being smoother than the female side. Preferably, one side of the film is corona discharge treated, and the treated side is disposed against the support regions of the backing member. Following aperturing in accordance with the teachings of the above-mentioned commonly-assigned, concurrently filed U.S. patent application Ser. No. 08/523,112 in one embodiment of the present invention, the corona treatment is on the male side of the film and the treated side is disposed against the support regions of the forming member. A surface active agent, i.e., a "surfactant" in a water-based solution is applied to the female side of the film and the film is rolled up so that surfactant is transferred from the female side of the film to the male side thereof. In accordance with another embodiment of the invention, the corona treated male side of the film is disposed against the support regions of the forming member, and following aperturing, surfactant is applied directly on the male side of the apertured film. In both embodiments, the resultant film is used with the corona-treated side facing the absorbent core of an associated absorbent article. It is preferred to have more surfactant on the corona-treated male side of the film to provide a gradient which enhances z-direction flow of liquid through the film, and which enhances x-y direction flow of liquid on the underside of the film.

These embodiments not only provide for efficient manufacture, but also result in a film having improved fluid distribution properties. In this regard, the resulting film also provides a wicking mechanism for spreading fluid in the x-y direction of the film on the side adjacent the absorbent core, which promotes more effective use of the absorbent core.

The method for forming an apertured film from a stretchable thermoplastic polymeric material in accordance with the present invention comprises the steps of providing an embossed starting film comprising stretchable thermoplastic polymeric material having an upper side and a lower corona discharge treated side. The method further comprises providing a backing member comprising localized support regions for supporting the starting film, recessed zones into which the film may be deformed by the application thereto of fluids, and means for allowing the applied fluid to be transported away from the backing member.

The starting film is supported on the backing member with portions of the lower side of the film being in contact with the support regions of the backing member and with the upper side of the film facing away from the backing member.

The method further comprises directing a fluid in the form of columnar streams from at least two sets of orifices against the upper side of the starting film in a zone of contact, i.e., a zone in which the film is subjected to the forces from the fluid streams. The orifices of the first set each have a diameter greater than ten mils and the fluid supplied thereto has a pressure less than 500 psig. to cause the formation of large sized holes in the starting film. The orifices of the second set each have a diameter less than or equal to ten mils and the fluid supplied thereto has a pressure of at least 500 psig. to cause the formation of micro-holes in the starting film, whereby a combination of large sized and micro-holes are formed in the starting film.

The present method further comprises moving the film from the contact zone, coating the upper side of the apertured film with a surface active agent, and winding the apertured film into a roll with the lower and upper sides being in surface-to-surface contact. By this surface-to-surface contact, at least a portion of the surface active agent is transferred from the upper side of the film to the lower side thereof.

Other features and advantages of the present invention will become readily apparent from the following detailed description, the accompanying drawings, and the appended claims.

BRIEF DESCRIPTION OF THE DRAWINGS

FIG. 14 is an end elevational view of the apertured film of FIG. 13 at a magnification of 15 times;

FIG. 15 is a top plan view of another apertured film at a magnification of 7.5 times;

FIGS. 18A and B are photographs taken at a magnification of 10× of apertured film formed in accordance with the invention, formed from an embossed starting film with the male side thereof against the associated forming member, wherein FIG. 18A is the side thereof against which water jets were directed.

DESCRIPTION OF THE PREFERRED EMBODIMENTS

Figure 1:
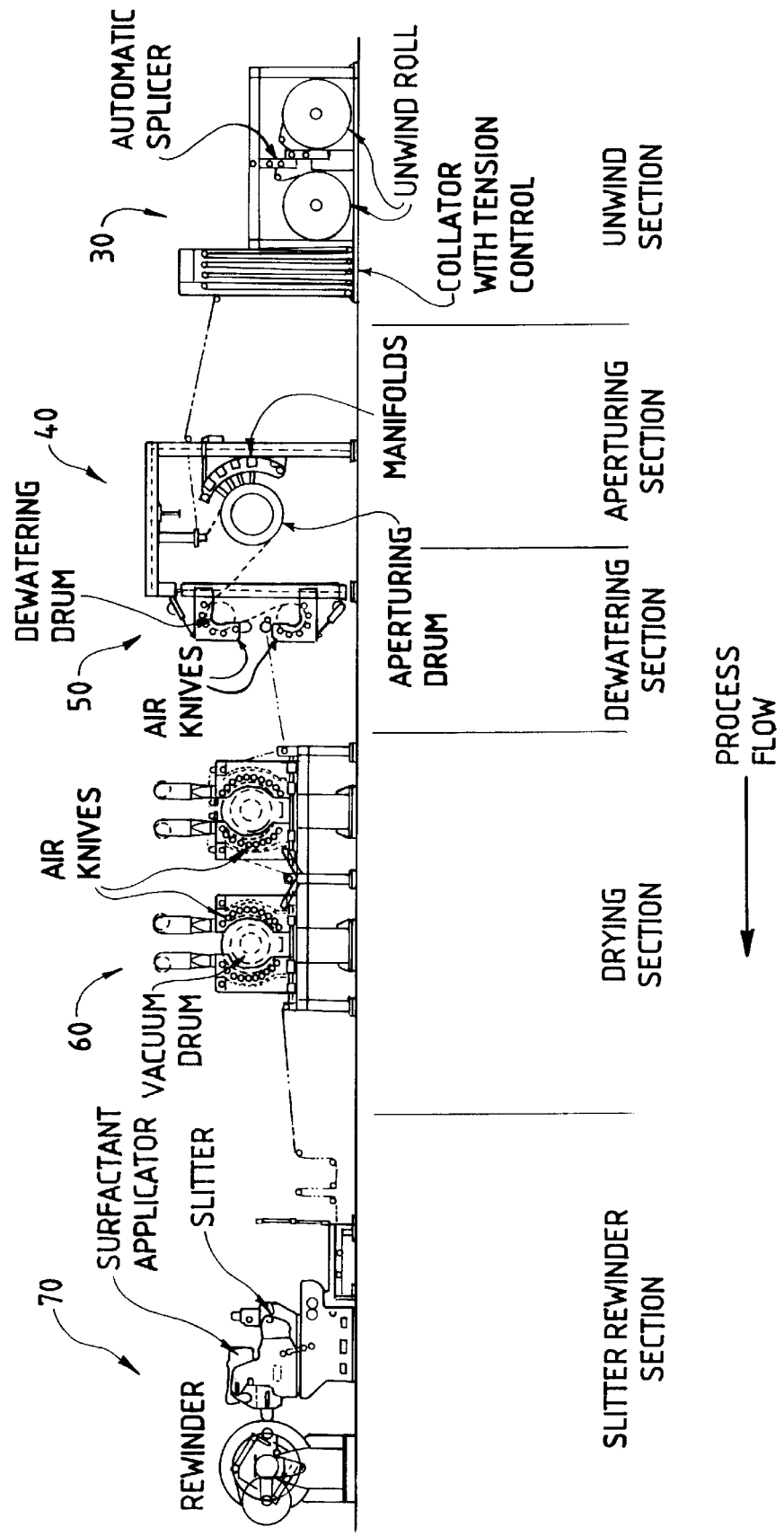
FIG. 1 is a schematic side elevational view of a production line for forming apertured film in accordance with the present invention.

While the present invention is susceptible of embodiment in various forms, there is shown in the drawings and will hereinafter be described presently preferred embodiments, with the understanding that the present disclosure is to be considered as an exemplification of the invention, and is not intended to limit the invention to the specific embodiments illustrated.

Referring now to the drawings, FIG. 1 is a schematic, side elevational view of one embodiment of a production line that may be utilized to produce apertured films in accordance with the teachings of the present invention. As is indicated by the direction arrow, the process flow proceeds from right to left in FIG. 1. As is shown in FIG. 1, the production line has five major stations; a film unwinding station 30, an aperturing station 40, a dewatering station 50, a drying station 60, and a slitting, rewinding, and surfactant application station 70.

Figure 2:
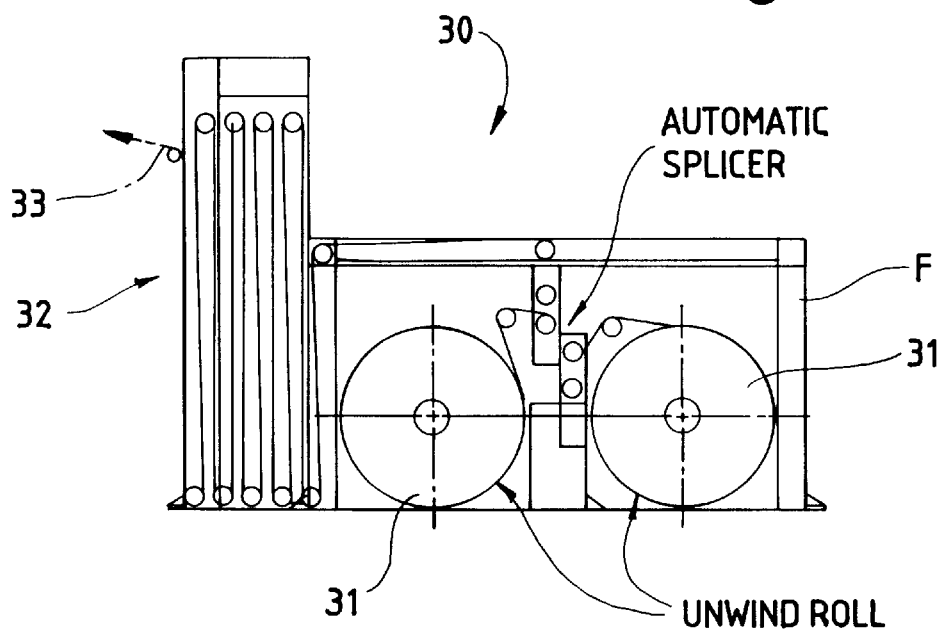
FIG. 2 is a schematic side elevational view, on an enlarged scale, of the unwind section of the apparatus for producing the apertured film of the present invention.

As shown in FIG. 2 in the film unwinding station, two rolls 31 of starting film material 33 are mounted for rotation on frame F. The film from rolls 31 is fed over guide rollers and into festoon 32 which has an automatic (closed loop) tension control system. Film 33, under suitable tension, e.g., between 0.1 to 1 pound per linear inch, emerges from festoon 32, and proceeds to the aperturing station 40.

While many different starting film materials are suitable for use in the present invention, one of the preferred materials is a polyethylene film commercially available from Exxon Chemical under product designation EMB-631. This film is an embossed, white pigmented polyethylene film. The polyethylene component consists of a blend of 40% by weight low density polyethylene and 60% by weight linear low density polyethylene. The film has 6.5% by weight titanium dioxide.

The starting film is embossed with a diamond pattern at 165 lines per inch to provide on one side of the film, referred to as the male side, a plurality of discontinuous observable protrusions separated by a continuous, interconnected grooved pattern. The other side of the embossed starting film, referred to as the female side, has a plurality of observable, cupped recesses separated by a continuous, interconnected rib pattern. The cupped recesses in the female side of the film are in respective registration with the protrusions on the male side of the film. The starting film is electrostatically treated with a corona discharge treatment on one side, preferably the male side. The film has an ultimate tensile strength of 1750 grams in the machine direction (with 500% elongation at break), and 1300 grams in the cross direction (with 650% elongation at break), as determined using ASTM test D-882.

The process for making the film of the invention may be either batch or continuous, generally similar to the batch and continuous processes disclosed in co-pending Ser. No. 08/417,404. The preferred embodiment is a continuous apparatus, as further disclosed herein.

Figure 3:
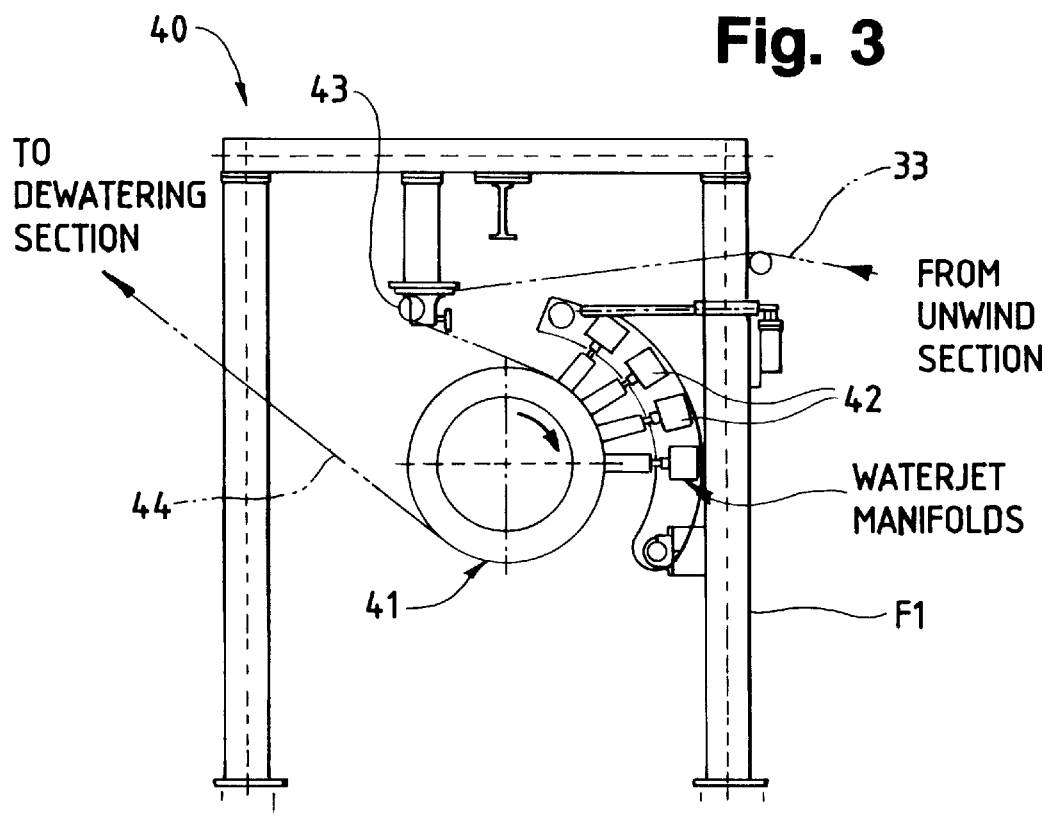
FIG. 3 is an enlarged side elevational view of the aperturing section of the apparatus used to form the apertured film of the present invention.

With reference to FIG. 3, the film 33 from the unwind station is shown entering aperturing station 40 at the right hand side thereof. Aperturing station 40 includes a honeycomb-type support drum 41 rotatably mounted on a frame F1. The drum 41 has a three-dimensional backing or forming member, described in detail hereinafter, mounted on its outer peripheral surface. Four water jet manifolds 42 are also supported on frame F1 and four suction slots, one for each manifold 42, are provided interiorly of the support drum, as is also hereinafter described in detail. The suction slots are mounted within the drum and are aligned with the water jet manifolds located outside of the drum. Each water jet manifold comprises a metallic strip, hereinafter sometimes referred to as an orifice strip, having a plurality of orifices having predetermined size and spacing. Specific examples of such orifice strips are described in more detail hereinafter. A given manifold 42 may comprise one or more orifice strips. The orifice size preferably remains constant for each strip. However, the orifice size may vary on a given strip. The distance between the lower surface of the orifice strip and the outer surface of the backing member of the aperturing drum is preferably in the range of between 0.50 to 1.0 inches.

Hot water under pressure is pumped to the manifolds 42, and the pressurized water exits through the plurality of orifices in the orifice strip in the form of columnar water jets. The water pressure in each manifold 42 may be separately regulated. The entering film 33 is trained over a guide roller 43, and then over the outer periphery of the three dimensional forming member mounted over the support drum 41, with the male side of the film being disposed against the forming member. The columnar streams of water exiting the orifice strips impinge on the film and cause the film to deflect downwardly into the recessed regions of the backing member mounted on the support drum, thereby causing the film to stretch and rupture into a multiplicity of irregular size holes. The now-apertured film 44 emerges from aperturing station 40 at the left-hand side thereof and passes to dewatering section 50.

Figure 4:
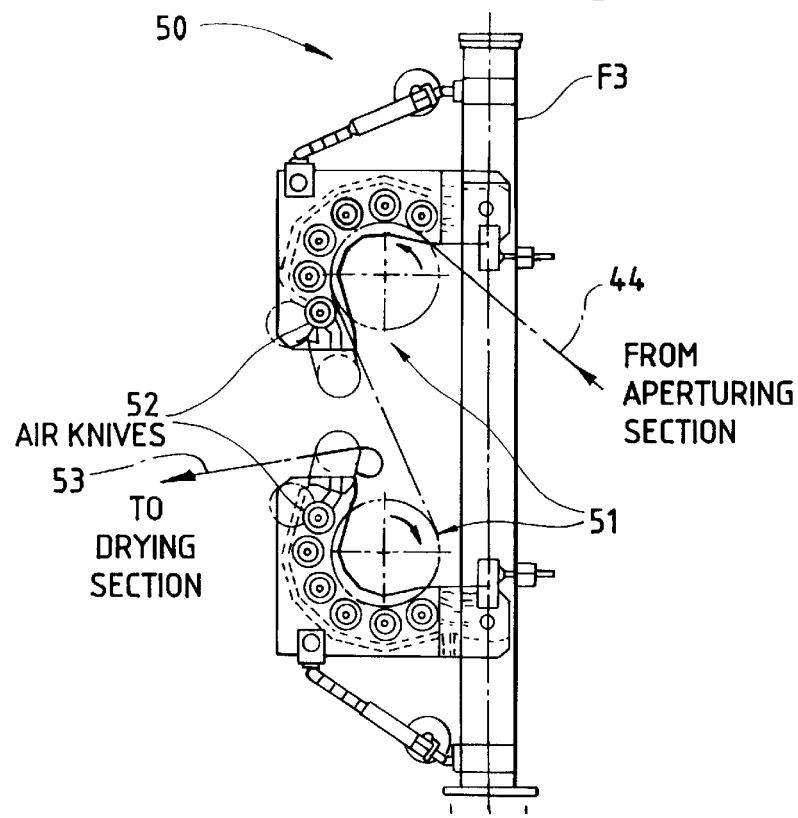
FIG. 4 is an enlarged side elevational view of the dewatering section of the apparatus used to form the apertured film of the present invention.

As is shown in FIG. 4, in the dewatering section 50, two dewatering drums 51 are mounted for rotation on frame F3. Drums 51 have a honeycomb configuration, and each drum has two vacuum slots associated therewith, capable of drawing vacuum up to 7 inches Hg. Twelve air knives 52 are provided, six air knives being provided for each drum 51. The suction slots associated with the dewatering drums 51 are located internally of the drums, whereas air knives 52 are located outside of the drums 51. Excess water is removed from the apertured film by the impingement of high velocity air from knives 52 and by suction through the suction slots in drums 51. Air knives 52 operate at an air temperature range between about 150°–180° F. Total air flow through the twelve air knives 52 is between about 1,000 to about 2,000 cubic feet per minute per linear foot of apertured film width. The dewatered film 53 emerges from the dewatering station 50, at the left-hand side thereof, and passes to the drying section.

Figure 5:
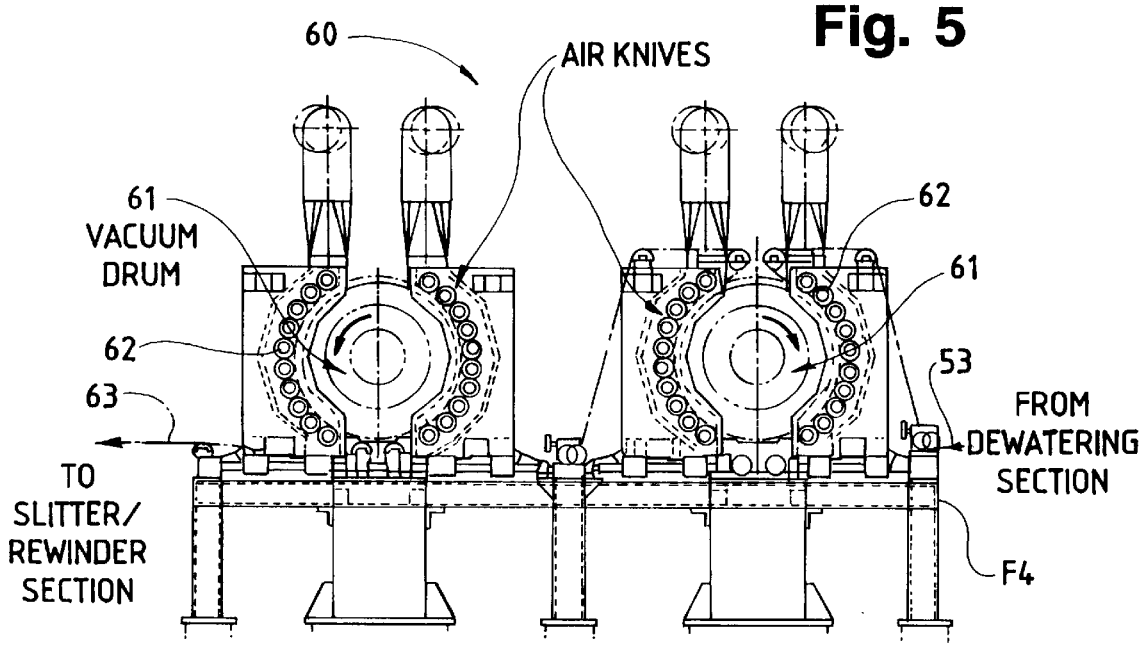
FIG. 5 is an enlarged side elevational view of the drying section of the apparatus used to form the apertured film of the present invention.

With reference to FIG. 5, the air drying station 60 is illustrated as including two vacuum drums 61 mounted on frame F4. Each drum 61 has a suction slot, which has an arc of 300° around the drum. Twenty air knives 62 are positioned outwardly of each vacuum drum 61 and the air knives 62 operate at a temperature between 150°–180° F. The combined air flow for all forty air knives 62 is between about 5,000 to about 7,000 cfm per linear foot of apertured film width. The pressure drop caused by the vacuum in drums 61 is about 2 inches of water measured across the film. The dried film 63 emerges from drying section 60 at the left-hand side thereof and passes to slitter/rewinder section 70.

Figure 6:
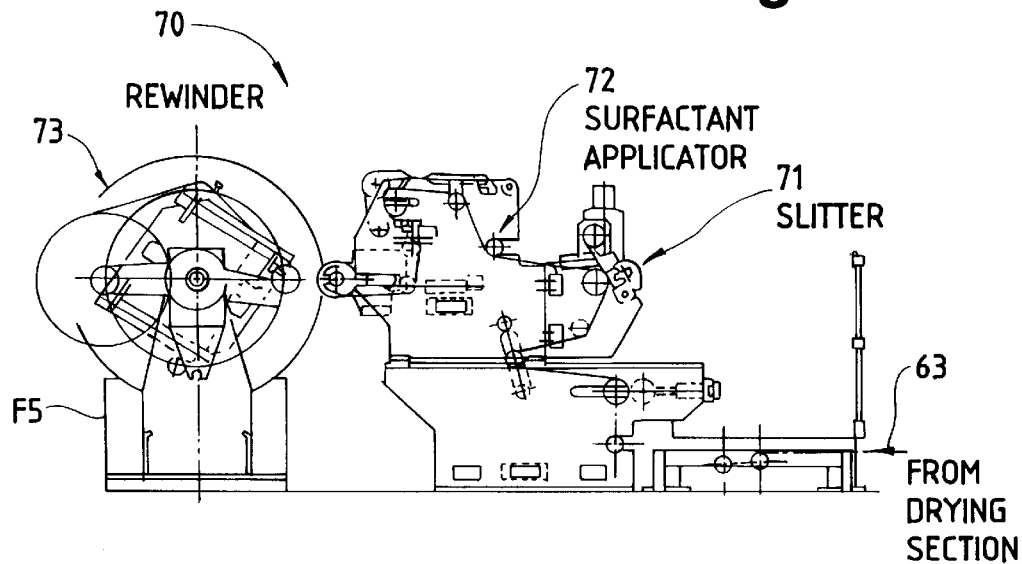
FIG. 6 is an enlarged side elevational view of the slitter/rewinder section of the apparatus used to form the apertured film of the present invention.

Referring now to FIG. 6, the film 63 from the drying section enters the slitter/rewinder station 70 at the right hand side thereof. A slitter 71, consisting of spaced score cut type slitting knives, cuts the dried apertured film to the desired width. The dried and slit apertured film then passes to a surfactant applicator 72, where a suitable surfactant, e.g., Tween, is applied to the film by kiss-coating. The surfactant is preferably provided in an aqueous solution consisting of about 48.8±1.5 percent surfactant. In an exemplary embodiment of the invention, the surfactant roller coating speed is 15±3 inches per minute. Preferably, the surfactant is applied to the female side of the film. Alternatively, the surfactant can be applied to the male side of the film, or to both sides of the film. The above-mentioned parameters result in a surfactant solution add-on of 0.25 mg/in$^2$±0.07. The surfactant coated slit apertured film, while still wet, then passes to a center driven rewind unit 73 mounted on frame F5 where the coated slit apertured film is wound into a roll.

When the film is wound into a roll, the male and female sides of the film come into contact with each other. The surfactant on one side is still wet when the film is wound into a roll, and some of the surfactant transfers to the other side of the film to which surfactant has not been applied. It is believed that when the surfactant is initially applied to the side of the film that is not corona treated (with no surfactant being applied directly to the corona treated side), approximately 65% or more of such applied surfactant transfers to the corona treated side of the film when the film is wound into a roll. It is believed that when the surfactant is initially applied to the corona treated side of the film (with no surfactant being directly applied to the non-corona treated side), approximately 25% or less of the applied surfactant transfers to the side of the film that is not corona treated when the film is wound into roll. Therefore, regardless of which side initially receives the surfactant application, a transfer of surfactant from one side to the other occurs when the film is wound into a roll, and the surfactant is distributed between the corona treated and non-corona treated sides such that the corona treated side retains approximately 65–75% or more, and the non-corona treated side retains approximately 25–35% or less, of the surfactant. The resulting apertured film material has a wettability gradient between the corona treated side and the non-corona treated side.

Testing of distilled water contact angles in Exxon EMB-631 film with male side corona treatment (unapertured) has resulted in a contact angle on the female side of 78 degrees when the surfactant was initially applied to the male side, and 76 degrees when the surfactant was initially applied to the female side. In both cases, the surfactant was applied in the manner in which it was applied to an apertured film, and the film was rolled up after application of the surfactant solution while the film was still wet. Transfer of the solution from the side on which it was initially applied to the opposite side of the film was as described above (i.e., approximately 65–75% of the surfactant was retained by the corona-treated side). The measured contact angle on the male side in both cases was zero degrees (0°). When no surfactant was applied, the contact angle was 102 degrees on the female side and 72 degrees on the male side. See Table 9 below.

Since the contact angle is an indicator of the wettability of the surface (with a lower contact angle indicating a higher degree of wettability), it is believed that a gradient in contact angle from the non-corona treated side to the corona treated side, as discussed above, facilitates the ability of the apertured film material to draw liquid from the non-corona treated side to the corona treated side. Further, it is believed that the reduction in contact angle to zero degrees (0°) on the corona treated side, which, in the absorbent articles of the present invention, is the side that normally faces the absorbent core of an absorbent article (such as a sanitary napkin) facilitates wicking for the spreading fluid in the x-y direction along the surface of the film that faces the absorbent core.

In prior art apertured films, it has been desirable to apply surfactant only to the side of the film facing the skin of the user of the absorbent article. The application of surfactant on the body facing side of the film facilitates the spreading of liquid on the body facing side of the film, and thereby increases absorption through the film and into the absorbent core. Further, the application of surfactant on the body side of the film provides a better tactile feeling for the user. A film processed according to the above method, wherein surfactant is distributed on both the body facing side and the absorbent core facing side of the apertured film, has not heretofore been thought to be desirable. Therefore, the film of the present invention has been found to have surprising, unexpected results regarding the ability of the apertured film to draw liquid from the body side to the absorbent side. See discussion regarding Tables 11–14 below.

Referring to FIGS. 7A–7E, the columnar jets of water are discharged from one or more orifice strips having a plurality of orifices. Preferably, the orifices are formed by drilling a precursor metallic strip to form cylindrical holes. However, it is anticipated that holes of various shapes may be used.

Figure 7A:
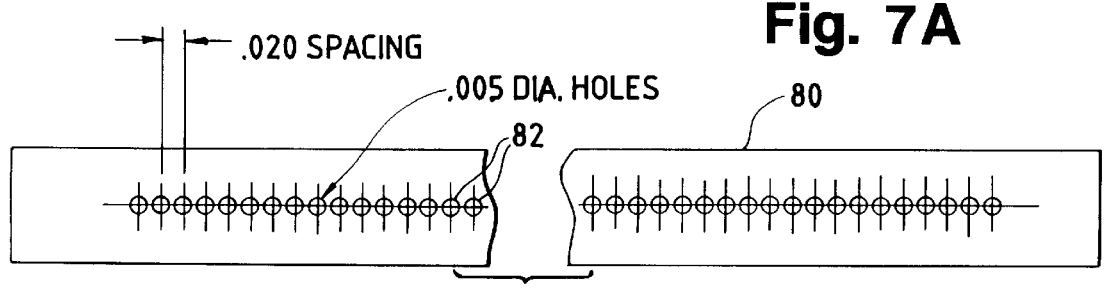
FIG. 7A is a schematic view of a orifice strip used in the apparatus to form one of the apertured films of the present invention.

FIG. 7A shows an orifice strip 80 for delivering columnar jets of water each having a relatively small cross-section to form micro-holes in the film. The orifices 82 in the manifold have a diameter of 5 mils (0.005 inch), and are spaced 0.020 inch apart. This manifold strip is available from the Nippon Nozzle Co., of Kobe, Japan.

Figure 7B:
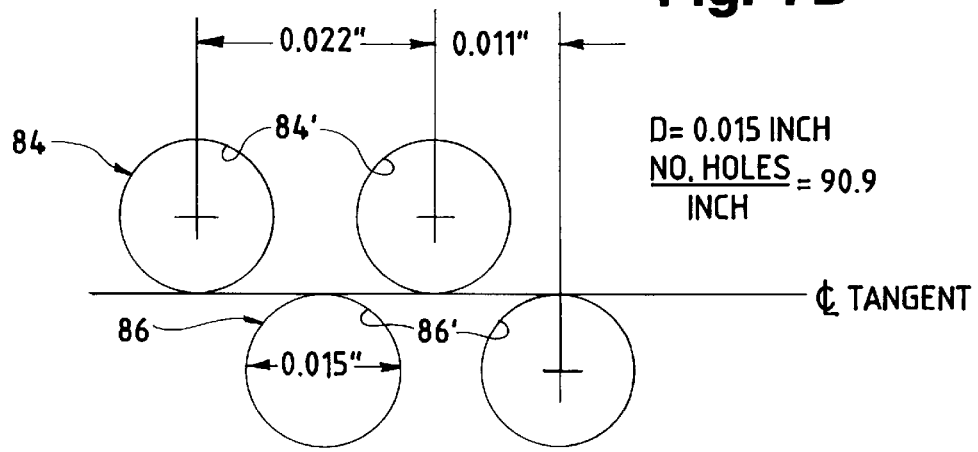
FIGS. 7B, C, D and E are enlarged views of orifice patterns which can be used in the apparatus to form the apertured films of the present invention.

FIGS. 7B–7E show orifice strips for producing columnar jets of water, each having a relatively large cross section, to form large sized holes in the film. FIG. 7B shows an orifice strip having two rows 84, 86 of orifices 84', 86' that are spaced apart on opposite sides of a center tangent line. The orifices in each row have a diameter of 15 mils (0.015 inch), and are spaced 0.022 inch apart, center-to-center. The spacing of the orifices in the top row is offset from the spacing of the orifices in the bottom row by 0.011 inch. The strip contains 90.9 orifices per inch.

Figure 7C:
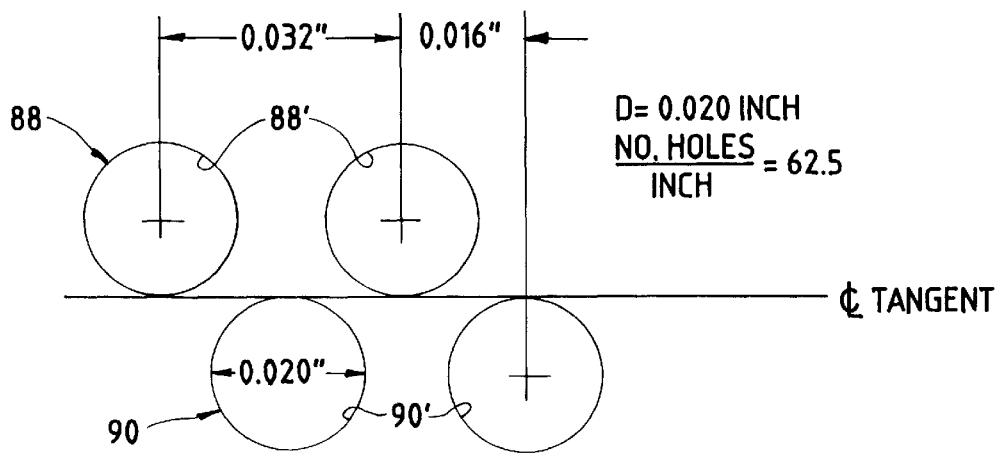

FIG. 7C shows an orifice strip having two rows 88, 90 of orifices 88', 90' that are spaced apart on opposite sides of a center tangent line. The orifices in each row have a diameter of 20 mils (0.020 inch), and are spaced 0.032 inch apart. The spacing of the orifices in the top row is offset from the spacing of the orifices in the bottom row by 0.016 inch. The strip contains 62.5 orifices per inch.

Figure 7D:
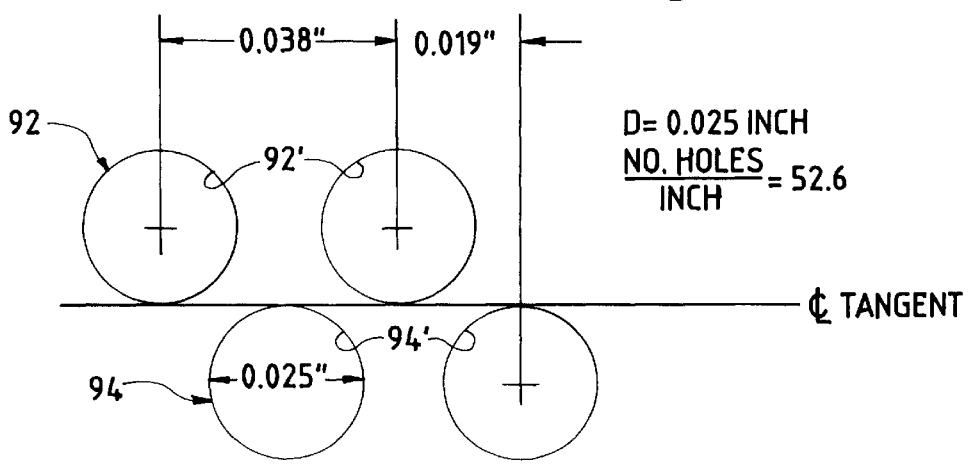

FIG. 7D shows an orifice strip having two rows 92, 94 of orifices 92', 94' that are spaced apart on opposite sides of a center tangent line. The orifices in each row have a diameter of 25 mils (0.025 inch), and are spaced 0.038 inch apart. The spacing of the orifices in the top row is offset from the spacing of the orifices in the bottom row by 0.019 inch. The strip contains 52.6 orifices per inch.

Figure 7E:
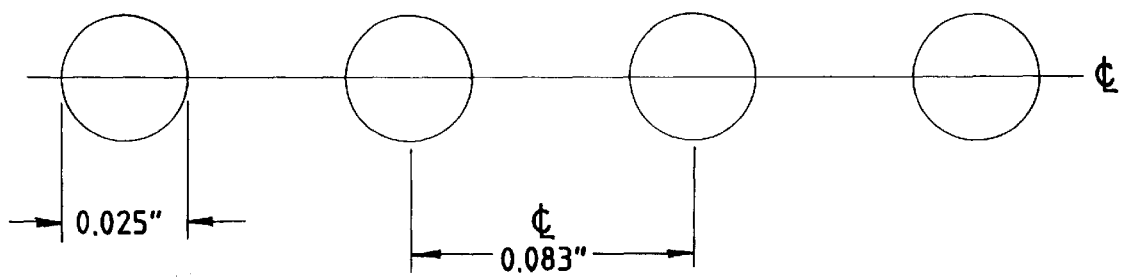

FIG. 7E shows an orifice strip for delivering columnar jets of water each having a relatively large cross-section for forming large sized holes in film. The orifices each have a diameter of 0.025 inches, and are spaced 0.083 inches, center-to-center. While the orifice strip shown in FIG. 7E is suitable for forming film in accordance with the present invention, use of orifice strips such as shown in FIG. 7B–7D is presently preferred for use in combination with one or more orifice strips having relatively small orifices for formation of micro-sized holes.

The small orifices (see FIG. 7A) preferably have a diameter under 10 mils. The larger orifices (see FIGS. 7B–7E) preferably have a diameter greater than 10 mils.

An apparatus for making apertured films of the present invention is described in detail in co-pending patent application Ser. No. 08/417,404. The apparatus for making the film of the present invention contains certain additional features, including a second set of orifice strips as discussed above with reference to FIGS. 7B–7E. The pressure of the water delivered to the small orifices is generally greater than 500 psig, preferably on the order of 500–1600 psig or higher. The pressure of water delivered to the large orifices is generally less than 500 psig, preferably on the order of 125–200 psig.

Figure 8:
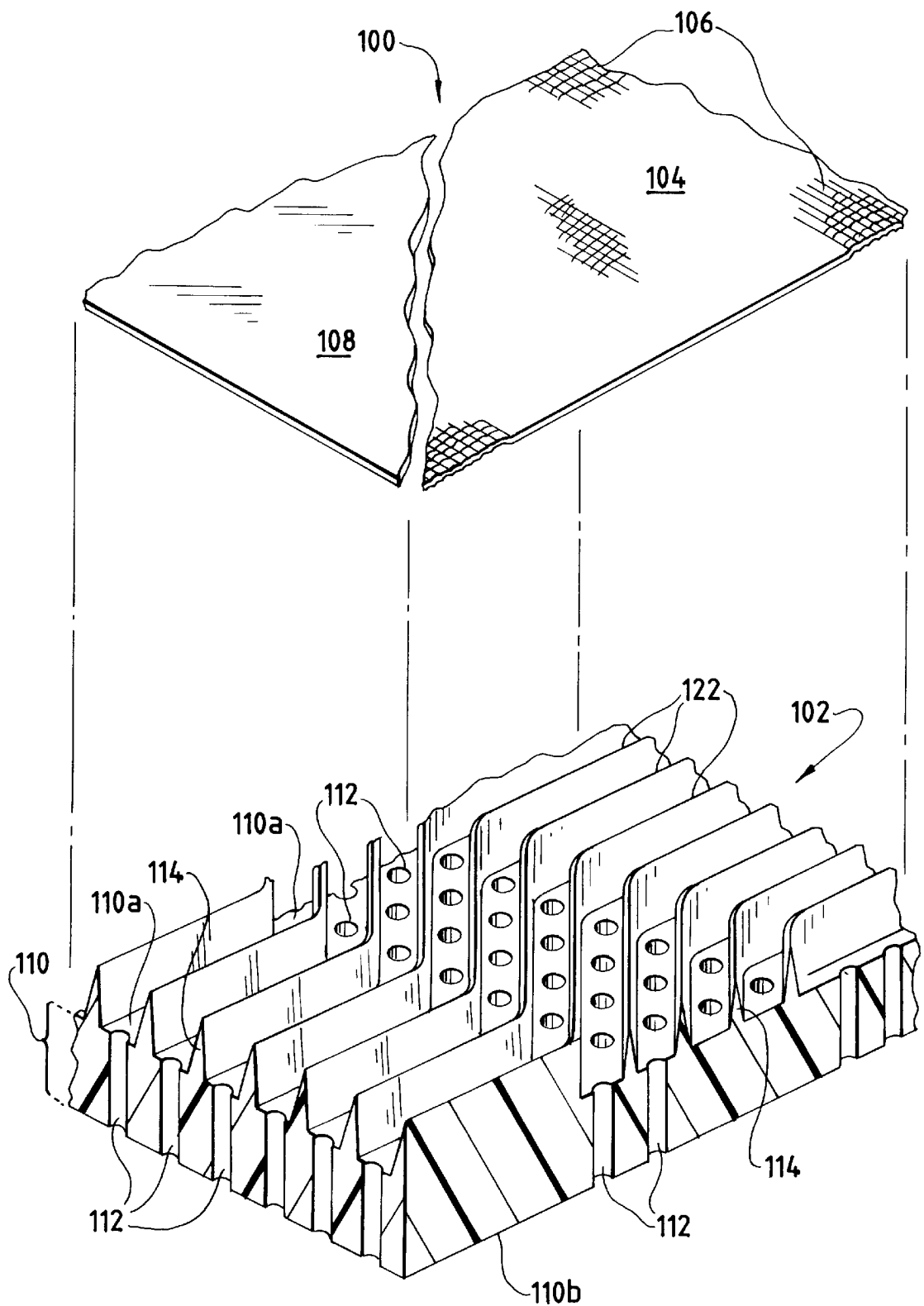
FIG. 8 is an exploded perspective view of a starting film positioned on a backing member for processing in accordance with the present invention.
Figure 9:
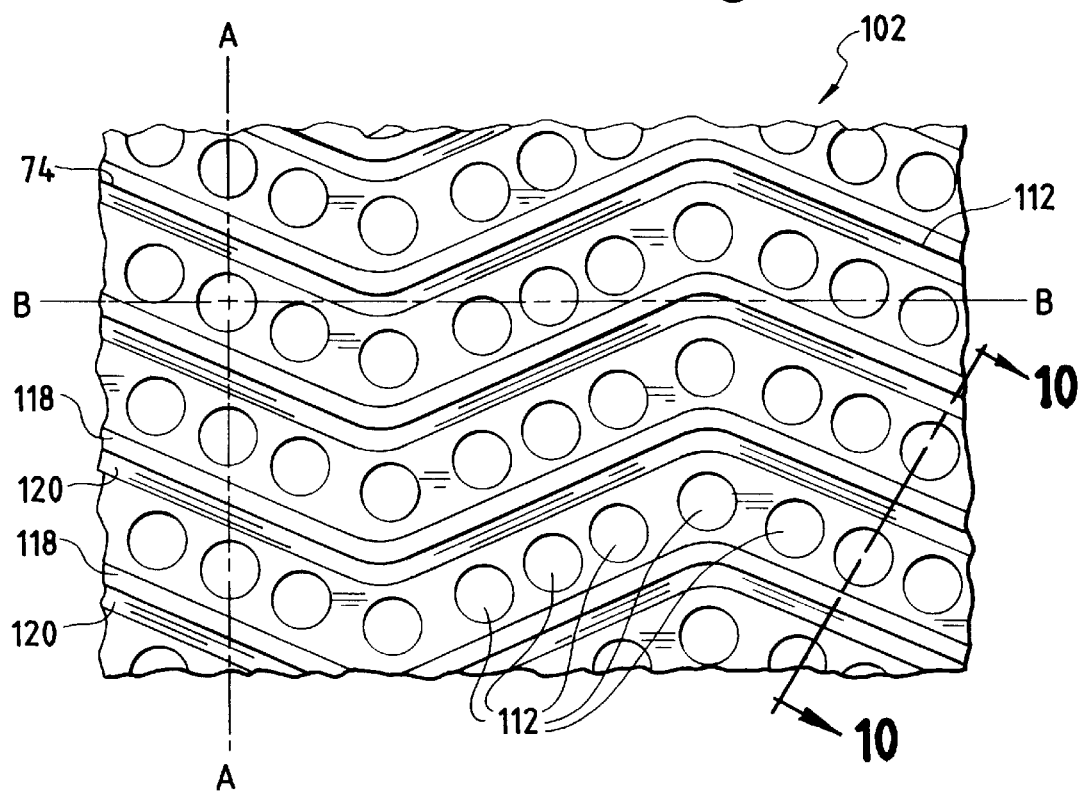
FIG. 9 is a top plan view of the backing member shown in the lower portion of FIG. 8.
Figure 10:
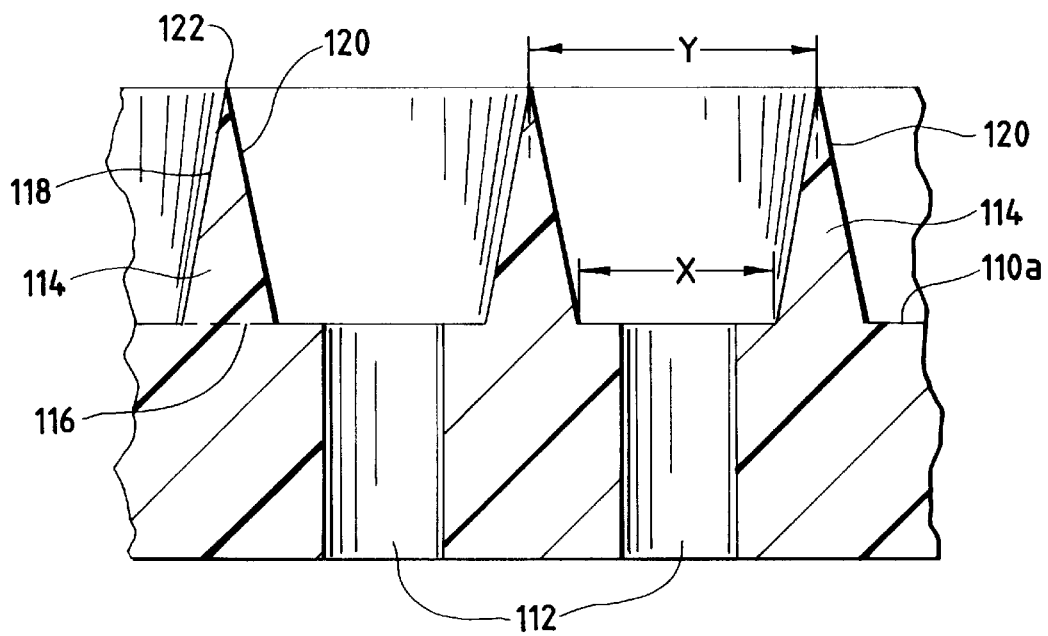
FIG. 10 is an enlarged cross-sectional view taken along line 10—10 of FIG. 9.

In a preferred embodiment, the aperturing equipment consists of a honeycomb type support drum, a three dimensional forming member, several water jet manifolds, and corresponding suction slots arranged interiorly of and sequentially along a section of the circumference of the drum. The forming member is an engraved sleeve, as shown in FIGS. 8–10, which is mounted onto the honeycomb support drum. The suction slots are mounted within the drum and they are lined up with the water jet manifolds located outside the drum. Each water jet manifold contains a metallic strip having a plurality of orifices. For a given manifold, the orifice size remains constant throughout the strip. The distance between the orifice strip and the surface of the engraved sleeve is preferably between 0.50 to 1 inch. The manifolds are pressurized by pumping in heated water. The pressurized water exits through the series of orifices in the orifice strip, thus creating substantially columnar water jets. The energy of the columnar hot water jets impinging on the film causes the film to contour toward the surface of the engraved sleeve thereby causing the film to stretch and rupture into a multiplicity of irregular size holes. The pressure and temperature of the water supplied to each manifold may be separately regulated. The process parameters are as follows:

Line Speed (yards/min): 50–200
Water Temperature: 155°–165° F.
Maximum Number of Manifolds Used: 3

Distance between Manifold Strip and Surface of Sleeve: 0.50"–1"

Low Pressure Manifold:
  Number of Manifolds: 1
  Orifice Size Range (inch): 0.0145 to 0.030
  Pressure (psig): 150±25
  Water Flow: 8.0±2.0 gallons per minute per inch of orifice strip (gpm/in)
  Suction Slot Vacuum (inch of Hg): 5.0±2.0 (–17±10.2 kPa)

High Pressure Manifold:
  Number of Manifolds: Maximum of 2
  Orifice Size Range (inch): 0.005 to 0.007
  Pressure (psig): 1,150±350
  Water Flow: 0.9±0.22 gallons per minute per inch of orifice strip
  Suction Slot Vacuum (inch of Hg): 5±3 (–17±10.2 kPa)

Manifold Usage Sequence:

The pressurized water jet manifolds and their associated orifice strips can be arranged in a variety of sequences relative to the direction of continuous travel of the film on the drum. Any of the following five sequences may be used to aperture the film:

1. Low Pressure, High Pressure
2. Low Pressure, High Pressure, High Pressure
3. High Pressure, Low Pressure
4. High Pressure, Low Pressure, High Pressure
5. High Pressure, High Pressure, Low Pressure Referring to FIGS. 8–10, the forming member is a three dimensional surface having a plurality of radially extending support elements that rise from the base of the forming or backing member. These elements are substantially similar to the corresponding elements disclosed in co-pending patent application Ser. No. 08/417,404.

FIG. 8 is an exploded perspective view of starting film 100 supported on backing member 102. The starting film may be either embossed or unembossed. Alternatively, a portion 104 of starting film 100 comprises embossments 106, and unembossed regions 108 as shown in the upper portion of FIG. 8.

Backing member 102 comprises a base portion 110 having an upper surface 110a and a lower surface 110b. Backing member 102 further comprises a plurality of apertures 112 running through the thickness of base 110 from upper surface 110a to lower surface 110b. As will be seen hereinafter, apertures 112 are provided to allow for removal of water during the manufacture of apertured film according to the invention. Backing member 102 also includes a plurality of radially-extending support elements 114. These support elements comprise a base 116 coinciding with the plane of upper surface 110a of portion 110 and a pair of angled side walls 118, 120 (best seen in FIGS. 9 and 10). Side walls 118, 120 extend outwardly from base 116 to meet at a land portion or ridge 122. Support elements 114 are aligned in parallel and spaced equidistantly from one another. They may run either parallel to, perpendicular to, or at any angle to the sides of the backing member. As shown in FIGS. 8 and 9, these support elements 114, when viewed in plan, are generally sinusoidal-like or wavy in configuration. It will be understood that the support elements may be provided in other configurations, e.g., straight-line, zig-zag and the like. A detailed description of the forming member is disclosed in co-pending patent application Ser. No. 08/417,404.

Figure 11A:
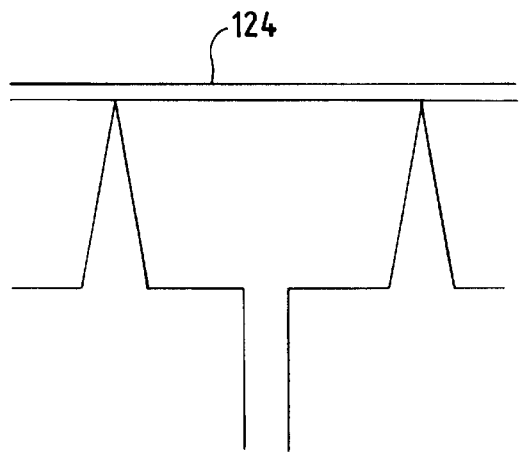
FIGS. 11A–D are views similar to FIG. 10 showing sequential stages in the drawing of the starting film to form apertures in accordance with the teachings of the present invention.
Figure 11B:
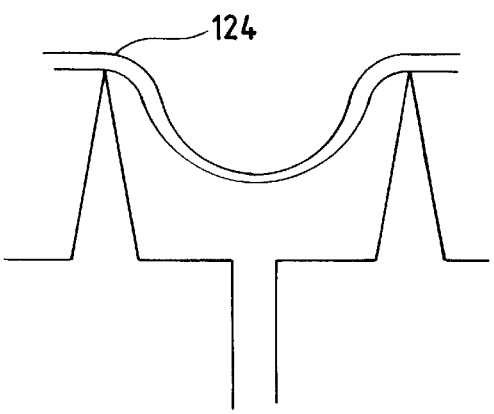
Figure 11C:
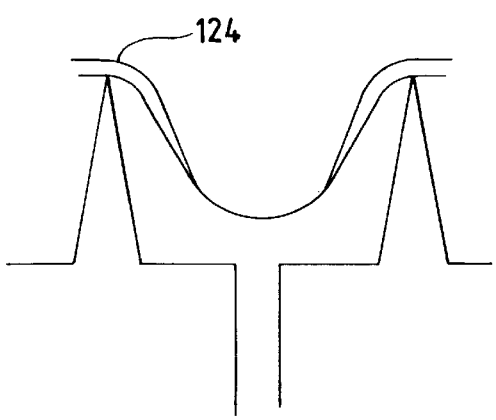
Figure 11D:
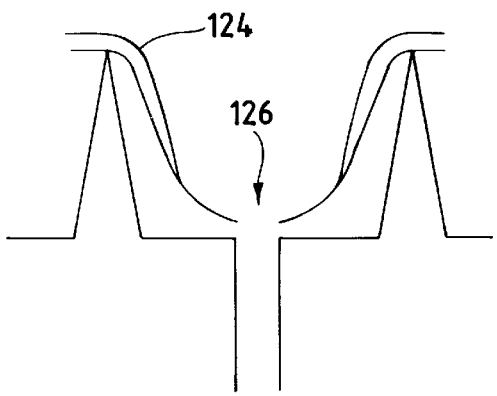
Figure 12:
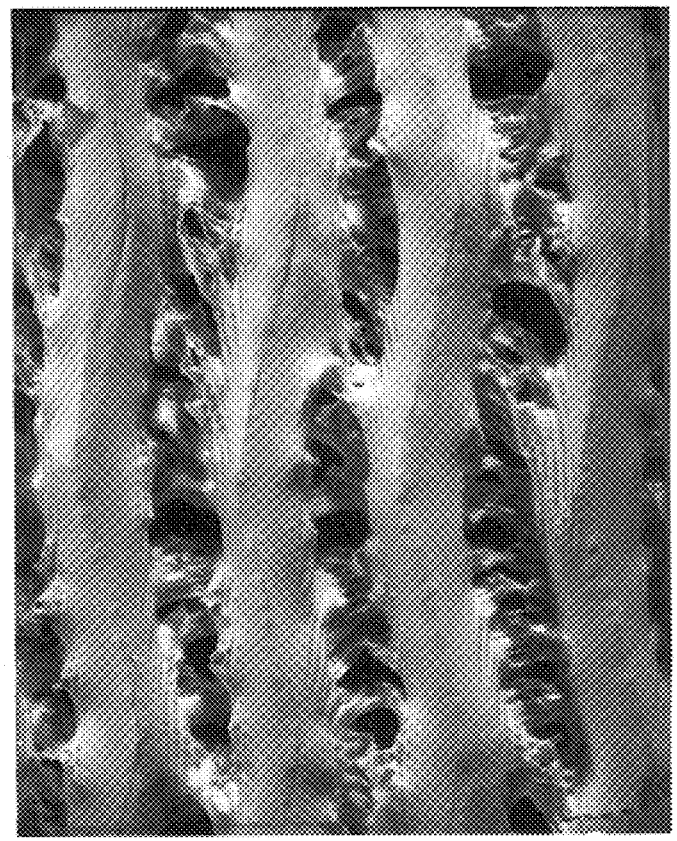
FIG. 12 is a photograph in top plan of an apertured film formed at a magnification of 7.5 times.
Figure 13:
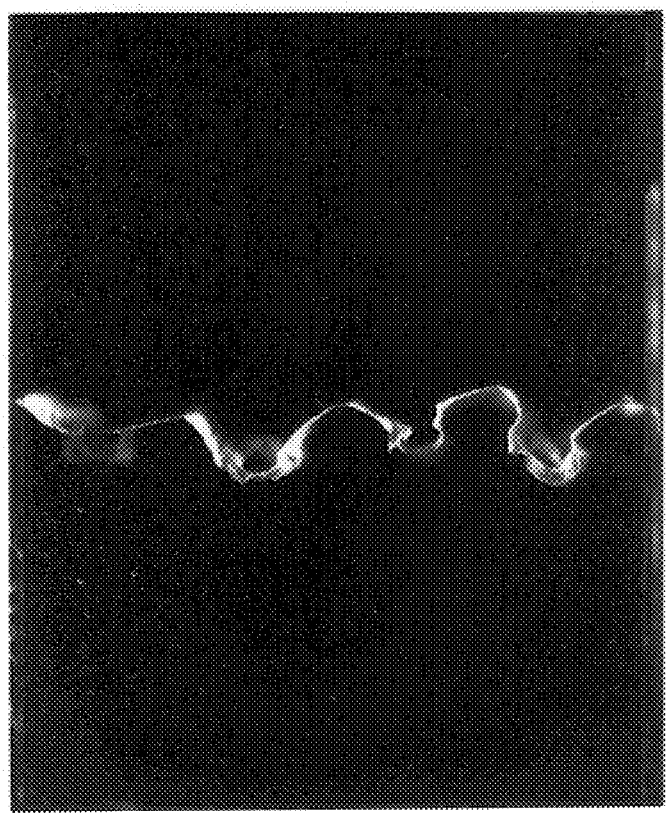
FIG. 13 is an end elevational view of the apertured film of FIG. 12.
Figure 16:
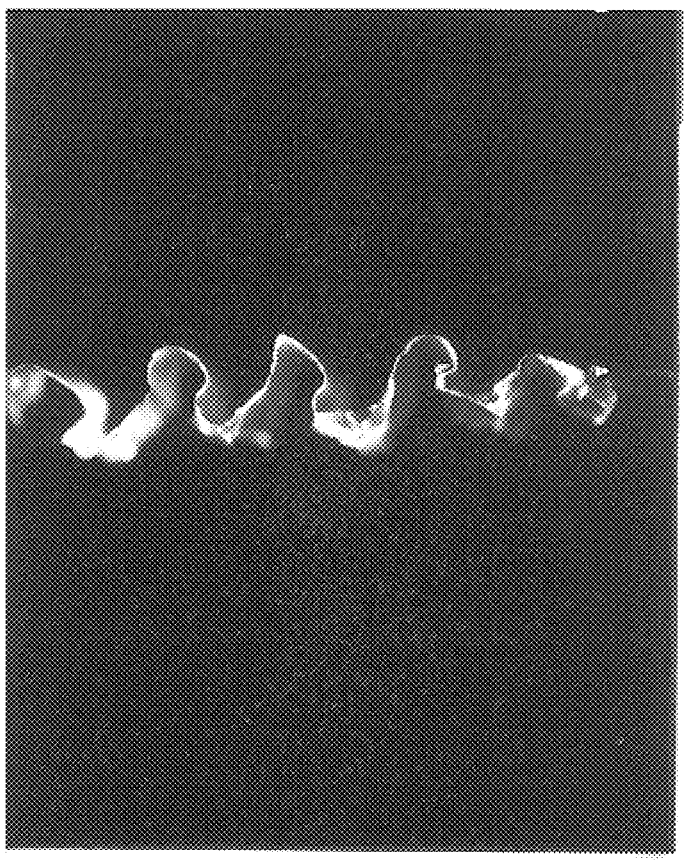
FIG. 16 is an end elevational view of the apertured film of FIG. 15.
Figure 17:
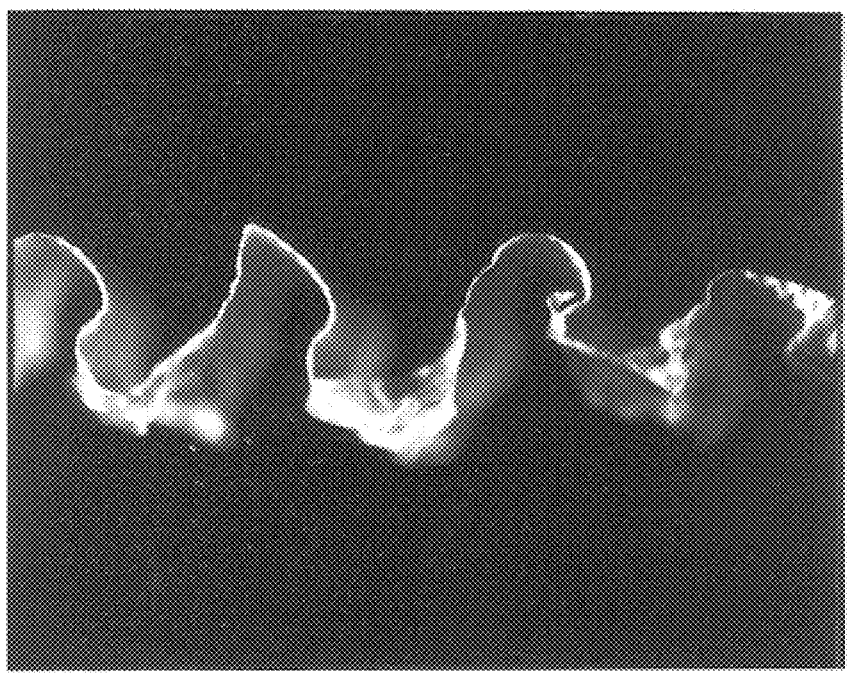
FIG. 17 is an end elevational view of the apertured film of FIG. 15 at a magnification of 15 times.
Figure 18A:
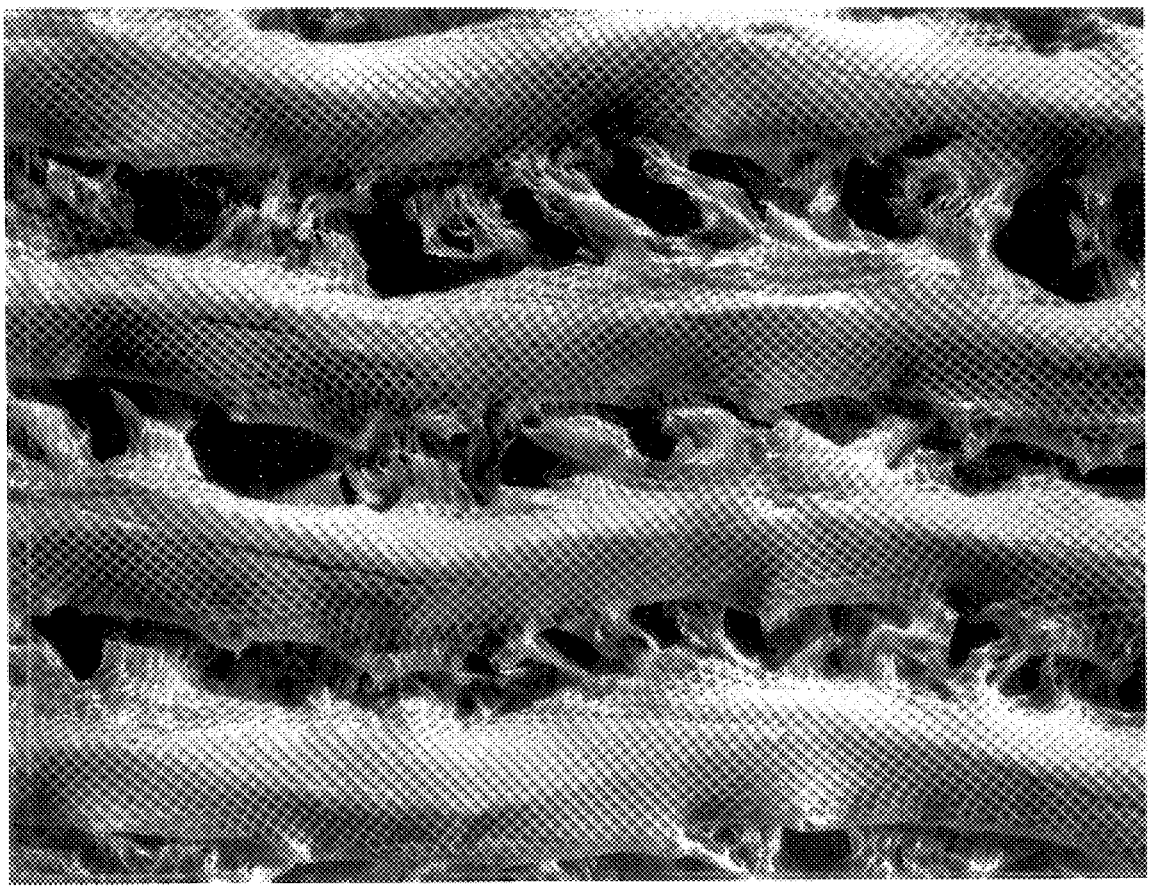
Figure 18B:
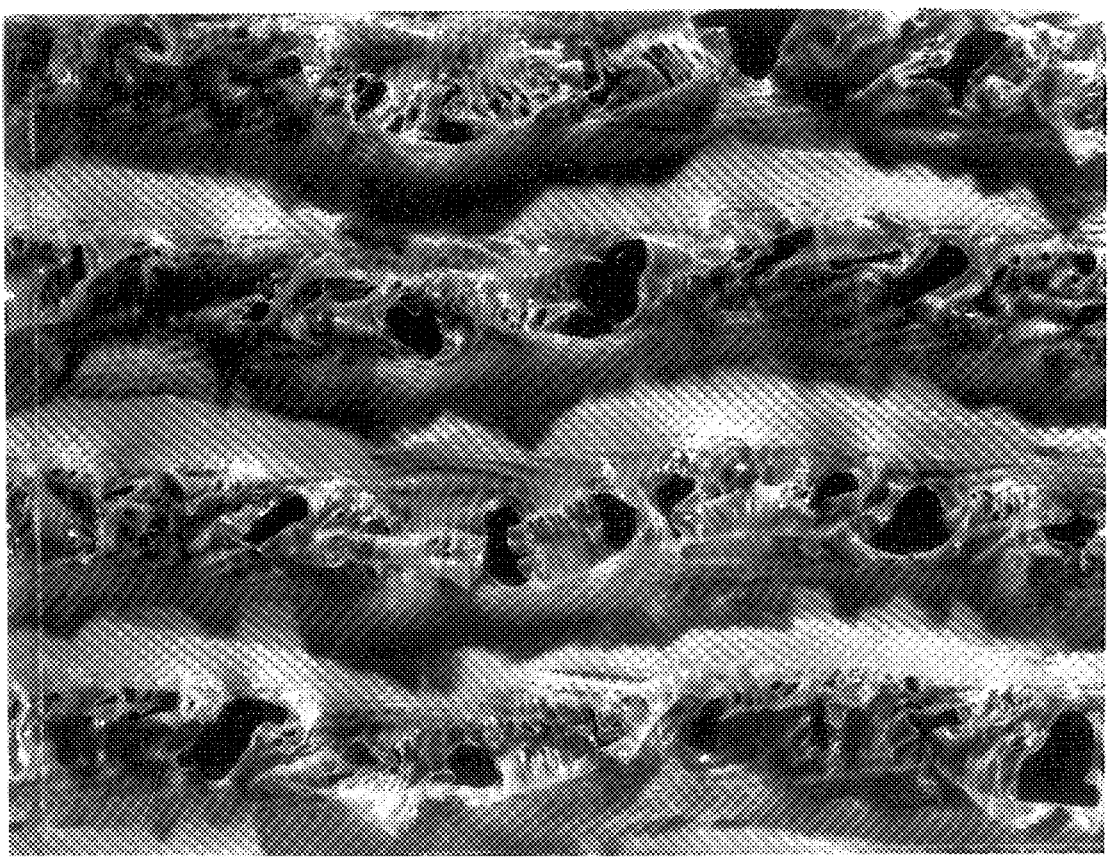
FIG. 18B is the side thereof positioned against the associated forming member.

Referring to FIGS. 11A–D, the progression of the drawing of the starting film 124 to form apertures in accordance with the teachings of the present invention are shown. Referring to FIG. 11A, the starting film 124 is initially laid on the backing member. Referring to FIG. 11B, the film 124 deforms in response to the application of columnar jets of water and is drawn (i.e., stretched) downwardly and partially into the space between support elements. Referring to FIG. 11C, as the film 124 is drawn, it becomes thinner. Referring to FIG. 11D, as the film is further drawn and becomes thinner, it begins to break apart and form holes 126. This process is further described in co-pending patent application Ser. No. 08/417,404, wherein the formation of micro-holes surrounded by micro-strips, or fibrils, of film material, is described.

Due to the vertical elements on the forming member, the film of the present invention is expanded (i.e., is given significant dimensionality in the z-direction relative to the original thickness of the precursor unapertured film) immediately as it comes off the process. In some prior art processes, expansion in the z-direction must be accomplished in a separate embossing step (see for example, U.S. Pat. No. 4,609,518). An expanded topsheet limits the contact between the wearer and the absorbent layer and thus enhances the feeling of dryness in products that incorporate it.

In the films, absorbent products and methods disclosed herein, the holes in the film include both micro-holes and large sized holes, or may include large sized holes only. It is believed that the micro-holes are formed primarily from the drawing of film material in response to application of columnar jets of water coming from the smaller orifices of the orifice strip discussed above. It is believed that the large sized holes, also formed from the drawing of film material, are formed primarily in response to application of the columnar jets of water coming from the larger orifices, rather than the smaller orifices, of the orifice strip discussed above.

The resulting apertured film has a combination of large sized holes or apertures having average EHD's of from about 7 mils to about 30 mils, and small sized apertures or holes, sometimes referred to as micro-sized holes, having average EHD's of from about 1 mil to about 7 mils. Such apertured films have an open area in the range of from about 3% to about 13%. It has been found that using orifice strips having orifices whose diameters range from about 10 to 25 mils results in the formation of apertures in the film having an average EHD of about 7 mils to about 17 mils. The fibrils surrounding and defining the micro-holes and the large sized holes are described in detail in co-pending patent application Ser. No. 08/417,404. The fibrils have lengths ranging from about 0.005 inch (0.013 cm) to about 0.05 inch (0.127 cm); widths ranging from about 0.001 inch (0.003 cm) to about 0.035 inch (0.089 cm); and thicknesses ranging from about 0.00025 inch (0.006 cm) to about 0.002 inch (0.005 cm). Photographs in FIGS. 12–18 show the combination of micro-holes and large sized holes of an apertured film.

The combination of large sized holes and micro-holes of the dimensions discussed above yield an improvement in the clean and dry properties of the film when used as a topsheet for a sanitary napkin. The resulting open area is in the range of 3 to 13%. In the prior art film having micro-holes only (see co-pending application Ser. No. 08/417,404), when 5 mil diameter columnar jets of water are used, the resulting apertured film has micro-holes with an average EHD of 3 mils, and has an open area of about 3%. The increased aperture size and open area in an apertured film having large sized holes in combination with micro-holes in accordance with the invention provides an improved level of aperture size and open area so as to strike an advantageous balance: large enough apertures to rapidly accept a flow of menstrual fluid and to allow it to pass through to the napkin's absorbent core, but small enough to mask the stain on the absorbent pad to give the consumer the perception of cleanliness. Thus, the absorbent products of the present invention made with the apertured films of the present invention have much improved clean and dry properties.

In a preferred embodiment of the invention, the starting film is apertured by large diameter, low pressure columnar water jets and small diameter, high pressure columnar water jets. This combination of jets at both high and low pressure produces larger apertures and greater open area than films made with small diameter high pressure jets alone. Films made by this embodiment also appear softer to the user than films made only with large diameter, low pressure jets.

Figure 19:
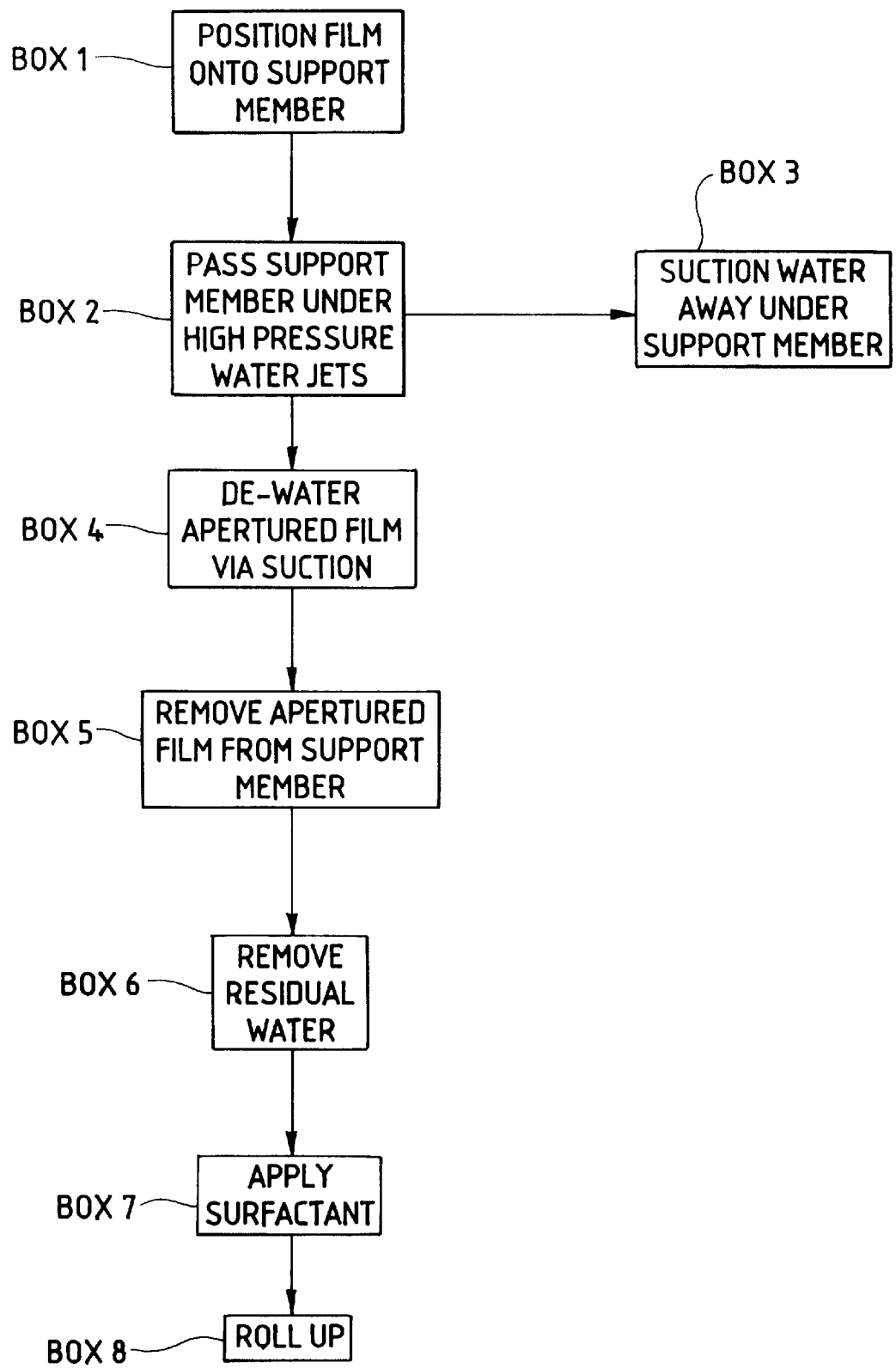
FIG. 19 is a block diagram showing the various steps of the process for producing the apertured film in accordance with the present invention.

FIG. 19 is a block diagram showing the several steps in the process for producing the novel apertured films of the present invention. The first step in the process is to position a piece of thin, stretchable film of thermoplastic polymer material on a backing or support member (Box 1). The support member with the stretchable film thereon is passed under high pressure fluid ejecting nozzles (Box 2). The preferred fluid is water. The water is transported away from the support member, preferably using a vacuum (Box 3). The film is de-watered, suction being preferred for this purpose (Box 4). The de-watered apertured film is removed from the support member (Box 5). Residual water is removed from the apertured film, e.g., by applying a stream of air thereto (Box 6). Surfactant is next applied to the apertured film (Box 7). The apertured film is then rolled up to await use as is or as a structural component of another product such as a sanitary napkin, disposable diaper or wound dressing (Box 8).

Figure 20:
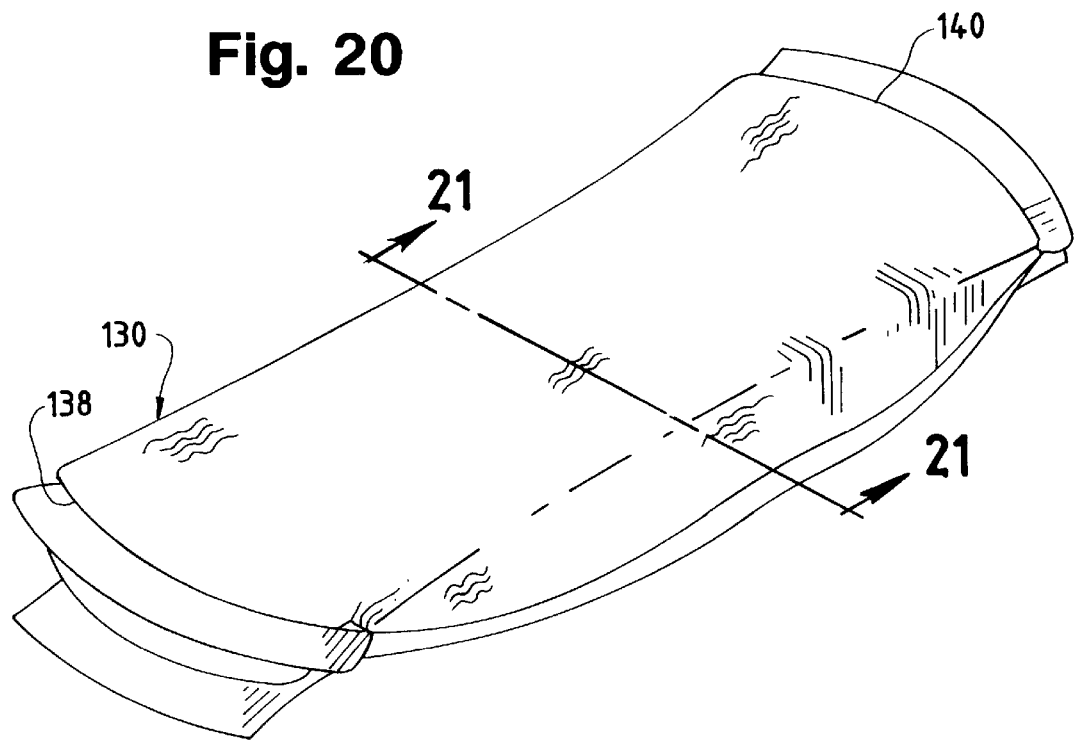
FIG. 20 is a perspective view of a sanitary napkin comprised of an apertured film according to the present invention.
Figure 21:
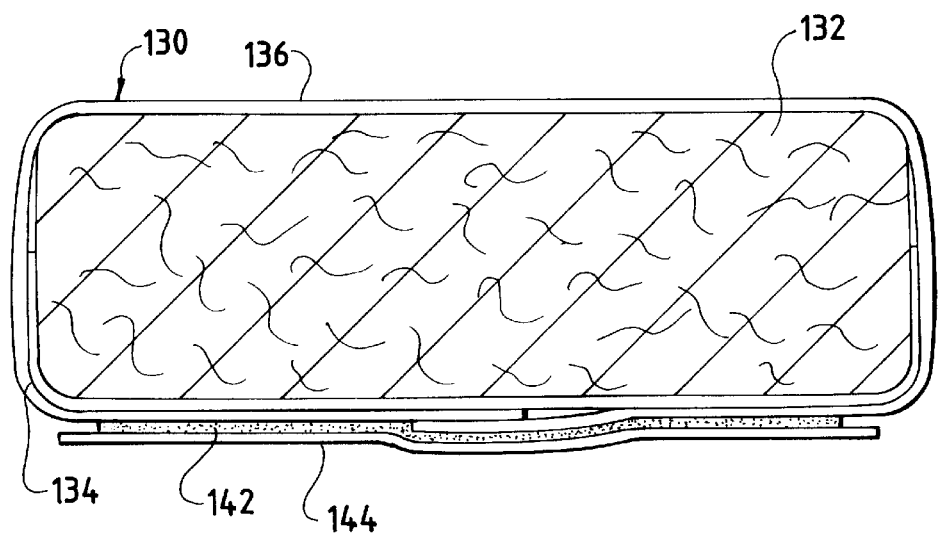
FIG. 21 is a view, in section, taken along line 21—21 of FIG. 20.

Referring to FIGS. 20 and 21, there is shown a sanitary napkin 130 comprising an absorbent core 132 of wood pulp fibers, a thin, fluid-impermeable barrier film 134 and a covering material 136 which may be any of the apertured films of the invention. Preferably, the covering film material has the structure shown and described herein. Barrier film 134, which may comprise, e.g., a thin film of polyethylene, contacts the lower surface of absorbent core 132 and runs part way up the longitudinal sides of the absorbent core. Covering material 136 has a length somewhat longer than the length of the absorbent core and is wrapped around the absorbent core and barrier film as shown in FIG. 21. The longitudinal edges of the cover material are overlapped and sealed together on the lower surface of the napkin in the usual manner. In the embodiment illustrated, the cover material is sealed to itself at the ends 138, 140 of the sanitary napkin. As illustrated in FIG. 21, sanitary napkin 130 has a layer of adhesive 142 for adhering the napkin to the undergarment of the user. Adhesive 142 is protected prior to use by a removable release strip 144.

EXAMPLE 1

In one embodiment of the apertured film in accordance with the invention, the starting material is an embossed film supplied by Exxon Chemical under the designation EMB-631, and having a thickness of 0.95 mils. This film is corona discharge treated on its male side. The film is placed on the forming member shown in FIGS. 8–10 which is mounted on a support drum as described in co-pending applications Ser. Nos. 08/417,404 and 08/417,408 to Turi et al. with the corona-treated male side of the film facing the forming member. Two manifolds for directing columnar streams of water at the film were used. The first, or upstream, manifold has the orifice configuration shown in FIG. 7D of the drawings, i.e., there are two offset rows 92, 94 of orifices 92', 94', each of the orifices having a diameter of 0.025 inches. The orifices are spaced a distance of 0.038 inches center-to-center to provide a total of 52.6 holes per inch. The second, or downstream, manifold has the orifice configuration shown in FIG. 7A of the drawings, i.e., there is a single row of orifices each having a diameter of 0.005 inches. The orifices are spaced 0.020 inches on a center-to-center basis.

There is a total of 50 such orifices per inch. Water having a temperature of 165° F. is supplied at a pressure of 165 psig to the first manifold, and at a pressure of 1400 psig to the second manifold. The film is passed under the manifolds at a speed of 435 feet per minute. The suction pressure inside the drum is minus 50 inches of water. The film is dewatered with the apparatus shown in FIG. 4 and is dried with the apparatus shown in FIG. 5. Following drying, the female side of the film is kiss-coated with a 48.8% solution of Tween-20 in water to a solution add-on of 0.25 mg/in$^2$. Subsequent rolling of the film effects transfer of the surfactant solution from the female side to the corona-treated male side. After the surfactant solution ultimately dries, the film has a bulk surfactant add-on (including all surfaces of the film) of 0.12 mg/in$^2$. The resulting apertured film has an air permeability of approximately 325 cubic feet per minute per square foot (cfm/ft$^2$) at a pressure differential ($\Delta$P) of 0.5 inches of water. The film has a measured open area of 6.24% and an average ECD of 10–11 mils. ECD (Equivalent Circular Diameter) is a calculated aperture diameter that is based on a measurement of the area of the aperture. The area is measured using the disclosed hardware and software for measuring EHD in co-pending patent application Ser. No. 08/417,404. The formula for ECD is $$ECD = \frac{\sqrt{4A}}{\pi},$$

where A is the measured area of an aperture. There is an average of 500 apertures per square inch. The bulk thickness is 14.5 mils.

The characteristics of the orifice strips used in the experiments described below are shown in Table 1:

TABLE 1

Characteristics of Orifice Strips

| Orifice Strip ID | Orifice Size (inches) | Number Of Rows Of Orifices Per Orifice Strip | Intra-Row Spacing Between Orifices (center-to-center, in.) | Number Of Orifices Per Strip Per Inch Of Orifice Strip |
|---|---|---|---|---|
| a | 0.005 | 1 | 0.020 | 50 |
| b | 0.010 | 2 | 0.015 | 133 |
| c | 0.015 | 2 | 0.022 | 90.9 |
| d | 0.020 | 2 | 0.032 | 62.5 |
| e | 0.025 | 2 | 0.038 | 52.6 |
| f | 0.025 | 1 | 0.083 | 12 |

Experimentation With Batch Formation Of Films

The batch film aperturing apparatus used in the experiment s reported in Table 2 below was similar to that shown in FIG. 3 of the drawings. However, only one water manifold 42 was used, and only one of the available vacuum slots was used. Each of the orifice strips labeled "b" through "f" in Table 1 was in turn mounted in the single water jet manifold and used to make one or more apertured films as shown in Table 2. The starting film and forming member were the same as those used in Example 1.

A piece of starting film was mounted to the outer surface of the fo r ming mem ber by a series of pins p rojecting from the forming member. The honeycomb support drum was rotated so that the mounted film was out of line with the single orifice strip. Vacuum was applied to the inside of the honeycomb support drum. Heated, pressurized water was supplied to the manifold. The honeycomb support drum motor was rotated to pass the starting film once under the orifice strip. The resultant film was removed from the forming member and air dried. Process conditions used to make films and the resultant film properties are shown in Table 2 below.

TABLE 2

Batch Film Aperturing Experiments

| Ex.# | Orifice ID | Water Pressure (psi) | Water Temp. (° F.) | Vacuum* (in.Water) | Film Speed (ft/min) | Open Area (%)** | Mean Equivalent Hydraulic Diameter (EHD)** (mils) |
|---|---|---|---|---|---|---|---|
| 1 | b | 350 | 160 | 60 | 150 | 3.6 | 10.7 |
| 2 | b | 550 | 160 | 60 | 150 | 6.5 | 10.3 |
| 3 | b | 1000 | 160 | 60 | 150 | 8.5 | 7.7 |
| 4 | c | 200 | 160 | 60 | 150 | 2.9 | 11.7 |
| 5 | c | 400 | 160 | 60 | 150 | 8.7 | 16.3 |
| 6 | c | 550 | 160 | 60 | 150 | 11.7 | 14.3 |
| 7 | c | 850 | 160 | 60 | 150 | 11.5 | 8.7 |
| 8 | d | 160 | 160 | 60 | 150 | 1.5 | 11.1 |
| 9 | d | 250 | 160 | 60 | 150 | 8.1 | 17.1 |
| 10 | d | 350 | 160 | 60 | 150 | 9.4 | 14.7 |
| 11 | d | 550 | 160 | 60 | 150 | 13.2 | 13.7 |
| 12 | e | 150 | 160 | 60 | 150 | 2.0 | 10.1 |
| 13 | e | 240 | 160 | 60 | 150 | 7.4 | 14.9 |
| 14 | e | 375 | 160 | 60 | 150 | 12.8 | 17.2 |
| 14a | f | 150 | 160 | 60 | 150 | 3.5 | 13.0(1) |
| 14b | f | 200 | 160 | 60 | 150 | 5.7 | 12.8(1) |
| 14c | f | 250 | 160 | 60 | 150 | 6.0 | 11.5(1) |

*vacuum value is inches of water below atmospheric pressure.
**Open Area and EHD were measured according to the method disclosed in co-pending application Ser. No. 08/744,744, which is incorporated herein by reference.
(1) = ECD The data indicate the following trends:

Increasing the fluid pressure with an orifice strip of a given size increases open area.

Increasing the orifice diameter increases open area at a given fluid pressure.

Due to stretch of material that occurs during the process of forming apertures, the weight per area of the film is reduced to about 0.47 oz/sq.yd, which is 65% of the initial film weight per unit area. When the 0.025 inch diameter orifice strips spaced at 0.038 inch, 0.050 inch, 0.062 inch and 0.075 inch of Table 8 were used, the open area decreased from 13.1% to 12.0, 11.2, and 10.1% respectively.

Experimentation With Continuous Formation Of Film

Additional embodiments of the film were made using the starting film, forming member and general procedure of Example 1. The characteristics of the strips are described in Table 1 above. All of the runs were made using water at 160° F., with the corona treated male side of the starting film facing away from the forming member. The number of strips used, and their characteristics and operating conditions are shown in the following table:

TABLE 3

Continuous Film Aperturing Experiments

| Experiment # | Orifice Strip #1 Orifice Strip ID | Orifice Strip #1 Pressure (psi) | Orifice Strip #2 Orifice Strip ID | Orifice Strip #2 Pressure (psi) | Orifice Strip #3 Orifice Strip ID | Orifice Strip #3 Pressure (psi) | Line Speed (ft/min) |
|---|---|---|---|---|---|---|---|
| 15 | d | 150 | | | | | 120 |
| 16 | d | 150 | a | 1000 | | | 120 |
| 17 | d | 150 | a | 1000 | a | 1000 | 120 |
| 18 | a | 1000 | | | | | 120 |
| 19 | a | 1000 | a | 1000 | | | 120 |
| 20 | a | 875 | a | 875 | a | 875 | 120 |
| 21 | a | 875 | a | 875 | a | 875 | 150 |
| 22 | a | 1000 | d | 150 | | | 120 |
| 23 | a | 1000 | d | 150 | a | 1000 | 120 |

Following air drying, the films were kiss-coated with an aqueous solution of Tween 20 surfactant at a concentration of 48.8% on the corona-treated male side to produce a bulk surfactant add-on of 0.12 mg/in$^2$ of film as described hereinabove in connection with Example 1.

The apertured films produced in these experiments were evaluated for air permeability, aperture size, open area, strikethrough and bending length (a measure of film stiffness). Tests were run according to the following methods well known in the art. Air permeability was tested according to ASTM D737. Film aperture size and open area were determined and used to calculate Equivalent Circular Diameter (ECD). Strikethrough is the time required for 5 cc of a test fluid to be absorbed through the film supported on ground fluff wood pulp. The test fluid is a mixture of 75% by weight of defibrinated bovine blood and 25% by weight of a 10% by weight aqueous solution of polyvinylpyrrolidone (GAF Povidone K-90). Bending length in the machine direction (MD) and cross direction (CD) were measured according to ASTM D1388. The properties of the film produced in continuous runs are shown in Tables 4–7 below.

TABLE 4

Continuous Apertured Film Properties-Air Permeability

| Experiment # | Air Permeability CFM/SQFT @ 0.5 in. H$_2$O ΔP) |
|---|---|
| 15 | 139.33 |
| 16 | 222.00 |
| 17 | 246.67 |
| 18 | 107.00 |
| 19 | 143.67 |
| 20 | 173.67 |
| 21 | 170.67 |
| 22 | 214.33 |
| 23 | 212.67 |

The data in Table 4 show that the combination of large diameter and small diameter orifices (experiments 16,17, 22 and 23) produces a more permeable, open film than films made with small diameter orifices alone (experiments 18–21). It is believed that the use of large diameter orifices, albeit used at lower water pressure, is the primary cause for the creation of large holes. Further, it is believed that the use of smaller diameter orifices is the primary cause for the creation of the smaller micro-holes.

TABLE 5

Continuous Apertured Film Properties-Aperture Size And Open Area

| Experiment # | Average Equivalent Circular Diameter (mils) | ECD Standard Deviation (mils) | Open Area (%) | No. Of Apertures/square inch |
|---|---|---|---|---|
| 15 | 16.46 | 10.12 | 4.55 | 197 |
| 16 | 8.62 | 9.22 | 5.34 | 515 |
| 17 | 7.48 | 8.47 | 5.34 | 715 |
| 18 | 4.65 | 2.66 | 2.31 | 1125 |
| 19 | 4.53 | 2.65 | 2.48 | 1283 |
| 20 | 4.00 | 2.25 | 2.38 | 1635 |
| 21 | 4.16 | 2.48 | 2.53 | 1519 |
| 22 | 6.49 | 5.59 | 4.15 | 806 |
| 23 | 6.88 | 6.18 | 4.88 | 856 |

The data in Table 5 show that the combination of large diameter and small diameter orifices (experiments 16, 17, 22, and 23) produce a film with larger aperture size and increased open area than films made with small diameter orifices alone (experiments 18–21).

Figure 22:
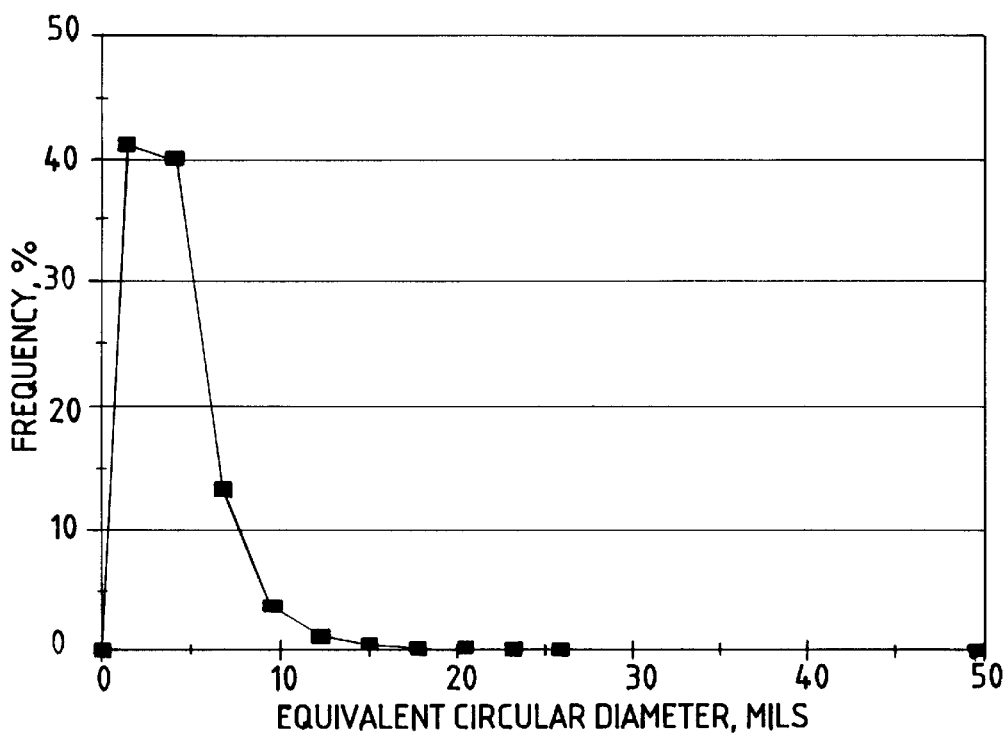
FIG. 22 is a graph depicting aperture size distribution in a sample of apertured film made at 875 psig. on an apparatus using three orifice strips each having a plurality of orifices, all of the orifices being 5 mils in diameter, said orifice strip being shown in FIG. 7A.
Figure 23:
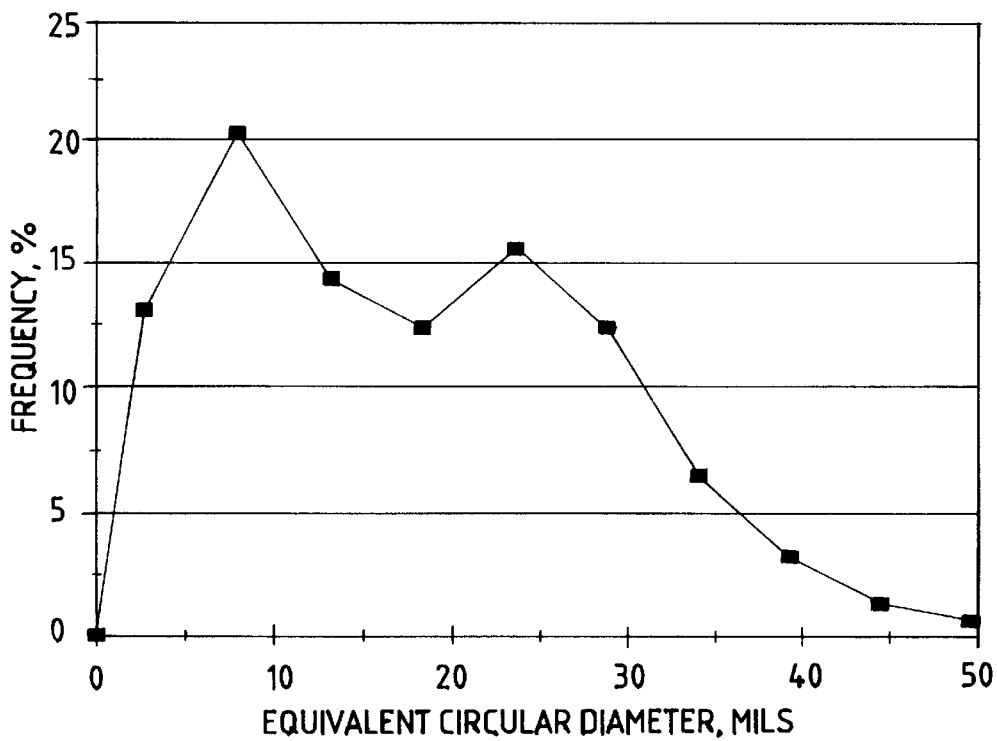
FIG. 23 is a graph depicting aperture size distribution in a sample of apertured film made on an apparatus comprising a single orifice strip having a plurality of orifices each 20 mils in diameter, said orifice strip being shown in FIG. 7C.
Figure 24:
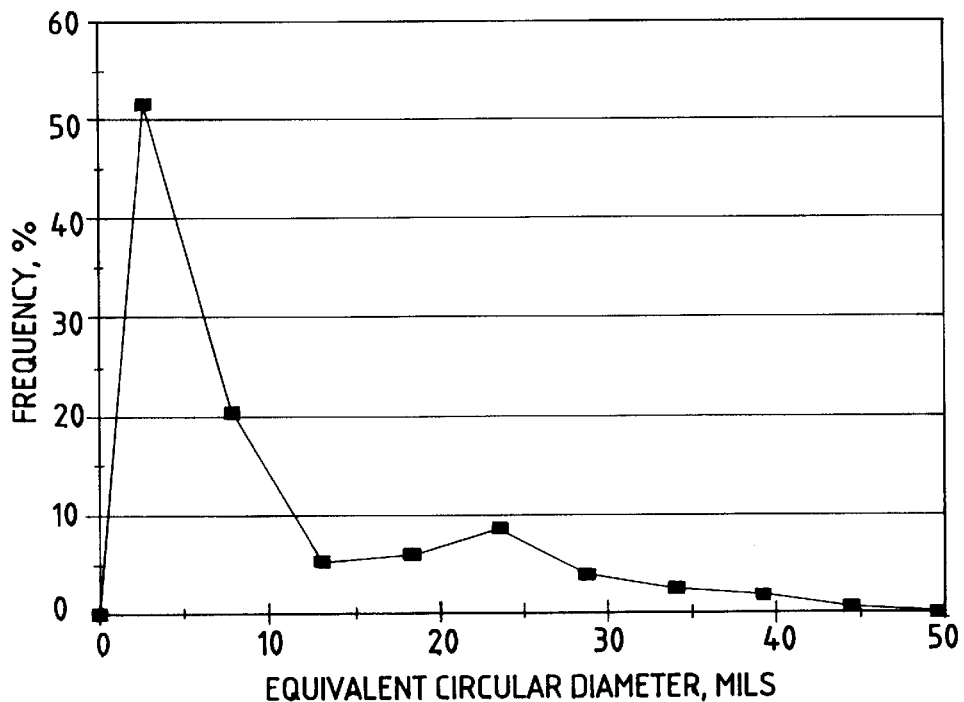
FIG. 24 is a graph depicting aperture size distribution in a sample of apertured film made on an apparatus comprising a first orifice strip (shown in FIG. 7C) having a plurality of orifices, all of which have a diameter of 20 mils, and a second orifice strip (shown in FIG. 7A), downstream of the first strip, wherein the second strip has a plurality of orifices all of which have a diameter of 5 mils.
Figure 25:
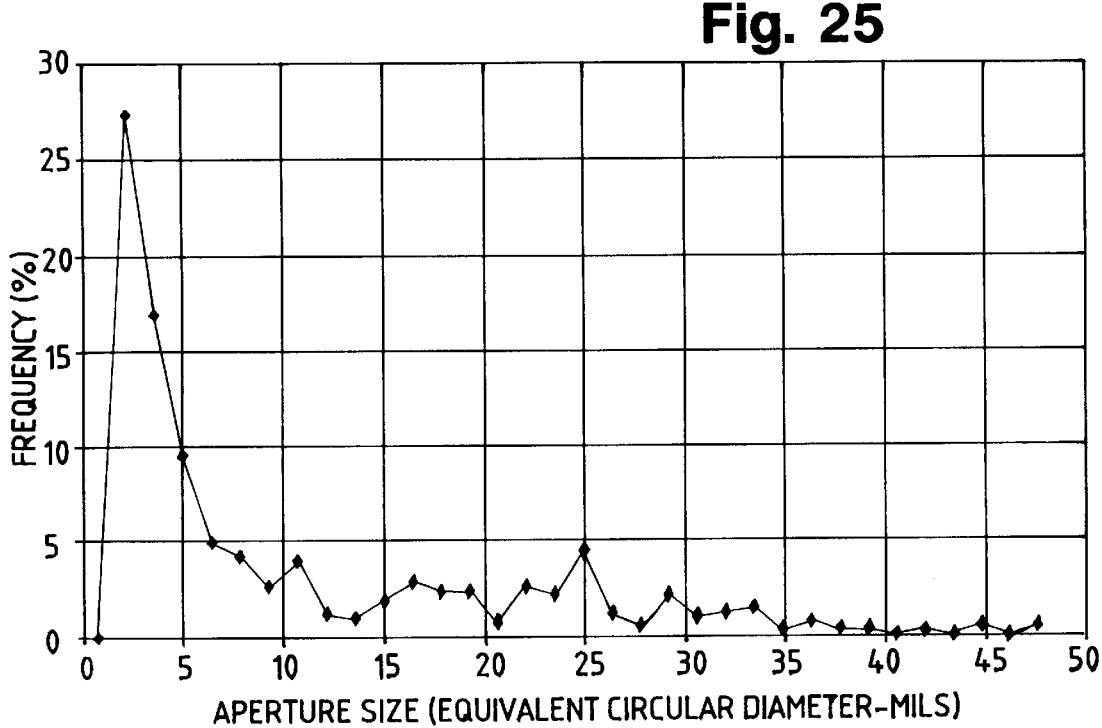
FIG. 25 is a graph depicting aperture size distribution in a sample of apertured film made in accordance with the invention.

FIGS. 22, 23 and 24 are graphs that show the aperture size distribution of films produced in these experiments with a 5 mil diameter orifice strip (Experiment No. 20), a 20 mil diameter orifice strip (Experiment No. 15), and the combination of a 20 mil orifice strip followed by a 5 mil orifice strip (Experiment No. 16), respectively (see Table 3 above). As seen from these graphs, the apertured films produced with orifice strips of different diameters have aperture sizes that reflect the effects of various of the individual orifice diameters. The film (Experiment No. 20) produced with only a 5 mil orifice strip has apertures most of which have a diameter under 10 mils (FIG. 22). The film (Experiment No. 15) produced by a 20 mil orifice strip only has a broader distribution of aperture diameters, with peak concentrations at approximately 9 mils and at approximately 23 mils (FIG. 23). The film (Experiment No. 16) produced by a combination of a 5 mil orifice strip and a 20 mil orifice strip has a distribution of aperture diameters that is primarily concentrated under 12 mils, and has a slight concentration of holes with a diameter of around 23 mils (see FIG. 24). These three graphs indicate that the 5 mil orifices create microholes primarily, that the 20 mil orifices create larger sized holes primarily, and that a combination of 5 mil orifices and 20 mil orifices creates a combination of micro-holes and large sized holes. Comparable data is shown in FIG. 25 which shows aperture size distribution in a sample of apertured film having micro-holes and large-sized holes in accordance with the invention that was made on a commercial production line.

TABLE 6

Continuous Apertured Film Properties-Strikethrough Time

| Experiment # | Strikethrough Time (sec) |
|---|---|
| 15 | 16.3 |
| 16 | 17.6 |
| 17 | 13.5 |
| 18 | 28.8 |
| 19 | 25.6 |
| 20 | 20.2 |
| 21 | 22.9 |
| 22 | 15.8 |
| 23 | 17.10 |

The data in Table 6 show that either large diameter orifices alone, or the combination of large diameter and small diameter orifices (experiments 15, 16, 17, 22 and 23) produce a film with faster strikethrough times than films made with small diameter orifices alone (experiments 18–21).

TABLE 7

Continuous Apertured Film Properties-Film Stiffness

| Experiment # | MD Bending Length (mm) | CD Bending Length (mm) |
|---|---|---|
| 15 | 22.8 | 6 |
| 16 | 26.3 | 6.5 |
| 17 | 22.3 | 6.5 |
| 18 | 27 | 6.3 |
| 19 | 26.8 | 5.5 |
| 20 | 26 | 9.5 |
| 21 | 25.5 | 8.5 |
| 22 | 23.5 | 5.8 |
| 23 | 27.30 | 8.0 |
| comparable commercial product | 21.8 | 14.8 |

The data indicate that the MD bending length of the films of experiments 15–23 is comparable to those of other commercial sanitary napkin plastic covers, and that the CD bending length of the films is lower than comparable commercial films. Hence, stiffness and expected comfort of the films of the present invention are expected to be comparable or superior to that of other commercial apertured films.

Figure 26:
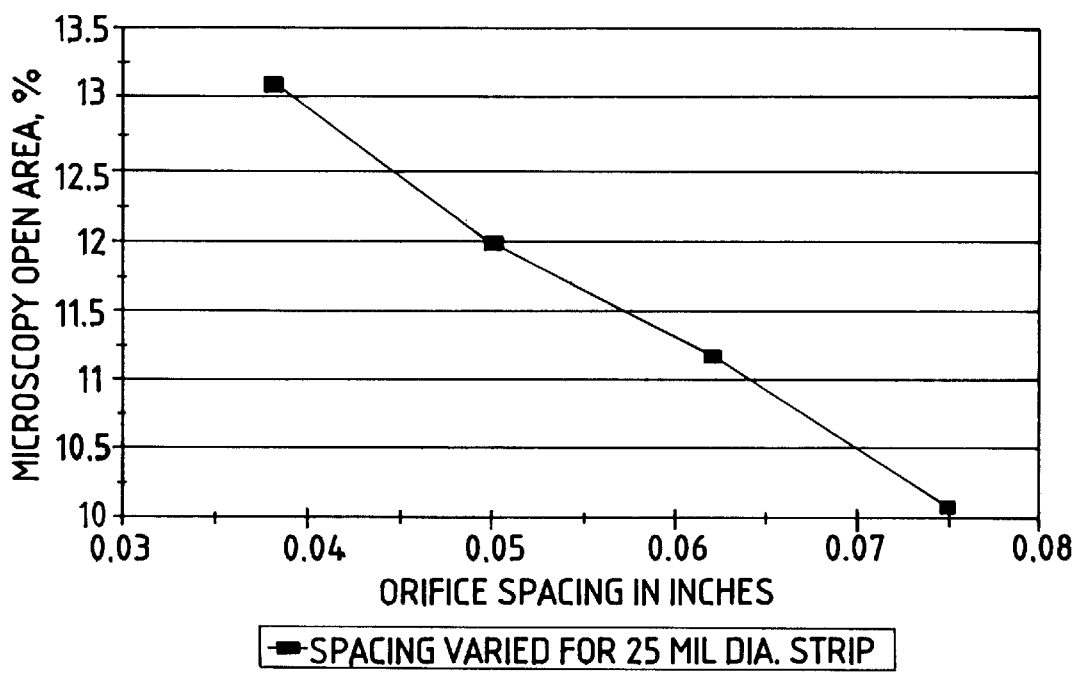
FIG. 26 is a graph depicting the results of comparison in which the spacing of the orifices comprising the orifice strip is varied.

Results of additional experimentation are shown in FIG. 26. In these experiments, the spacing of the orifices was varied to determine the effect on film open area. Two water jet manifolds were used in these experiments. The first, or upstream, manifold had one orifice strip with two rows of orifices on respective sides of the longitudinal center line of the strip, the two rows of orifices being offset as shown in FIGS. 7B–7D, i.e., the offset distance was one-half the intra-row, center-to-center spacing of the orifices. All orifices had a diameter of 0.025 inch. The center-to-center spacing of the orifices for each experiment was varied as reported in Table 8.

The second, or downstream, manifold had one orifice strip with a single row of orifices therein. The orifices each had a diameter of 0.005 inch and were spaced 0.020 inch on a center-to-center basis. Water was supplied to the first manifold at 150 psig. Water was supplied to the second manifold at 1000 psig. The film traveled at 150 ft/min. The drum vacuum was 60 inches water. The following Table 8 indicates the open area, number of apertures per $in^2$, ECD and air permeability for the resulting apertured films.

TABLE 8

| Film Number | Large Orifice* Spacing, inch | Open Area, % | Number of Apertures | Equivalent Circular Diameter, inch | Air Permeability |
|---|---|---|---|---|---|
| 24 | 0.038 | 13.1 | 914 | 0.0099 | 505 |
| 25 | 0.050 | 12.0 | 1136 | 0.0085 | 476 |
| 26 | 0.062 | 11.2 | 1151 | 0.0081 | 465 |
| 27 | 0.075 | 10.1 | 1299 | 0.0072 | 435 |

*Two rows of 25 mil diameter orifices.

Air permeability was measured per ASTM D737; results are reported in Table 8 in cubic fees per minute per square foot of film. The air permeabilities of film apertured at 150 psig and 150 ft/min. were 310 cfm/sf for the 25-mil diameter orifice strip (only) (0.038 inch spacing) control, which decreased nearly linearly to 245 cfm/sf for the 0.075 inch spacing. When the 5-mil diameter orifice strip was added, the air permeability increased to 505 cfm/sf for the control spacing. There was a nearly linear decrease with spacing to a value to 435 cfm/sf at 0.075 inches. At 150 ft/min., the combination of the large diameter, 25 mil diameter control strip with the 5-mil strip provides about 195 cfm/sf beyond the measured air permeability of the large hole strip alone. The above data indicates that as large orifice spacing increases, fewer large-sized holes are produced, and the open area is accordingly reduced.

Wettability Of Non-Apertured Film With Surfactant Treatment

The following Table 9 shows the results of testing of Exxon EMB-631 with the male side having been corona discharge treated. The contact angle and surfactant distribution between the male and female sides, after roll-up, were tested. The contact angle was also measured on the male and female s ides when there was no surfactant supplied to the film.

TABLE 9

Distilled Water Contact Angles And Surfactant Distribution of Processed Exxon EMB-631 Films EMB-631 With Male Corona Treatment

| | No Surfactant Treatment | | Male Surfactant Treatment | | Female Surfactant Treatment | |
|---|---|---|---|---|---|---|
| | Male | Female | Male | Female | Male | Female |
| Contact Angle | | | | | | |
| aver. | 72 | 102 | 0 | 78 | 0 | 76 |
| std. dev. | 6 | 7 | 0 | 11 | 0 | 3 |
| Surfactant Distribution | | | | | | |
| aver. | 0.000 | 0.000 | 0.869 | 0.249 | 0.775 | 0.429 |
| std. dev. | | | 0.107 | 0.089 | 0.093 | 0.040 |

The above data indicates that corona discharge treatment reduces the contact angle of the film. The above data further indicates that the application of surfactant to either the corona treated or non-corona treated side, followed by a roll-up of the film results in a distribution of surfactant wherein over 65% of the surfactant ends up on the corona treated side. Further, the data shows that the application of surfactant lowers substantially the contact angle on the non-corona treated side, and lowers the contact angle on the corona treated side to zero. It is believed that the gradient in the contact angle, wherein the contact angle is substantially lower on the corona-treated side of the film, establishes a desirable "hydrophilicity gradient" that facilitates z-direction flow through the film. Further, the lowering of the contact angle on both sides of the film is believed to substantially improve x and y direction flow along the top and bottom surfaces of the film. In a sanitary napkin in which the corona-treated side of the apertured film faces the absorbent core, improved spreading of fluids in the x and y direction is expected to enhance the z-direction flow of fluids to the absorbent core that is adjacent the lower surface of the film.

Top surface contact angle, bottom surface contact angle, film aperture pattern, and embossing pattern can be combined in various ways to yield the desired fluid distribution properties. Employing a cupped female emboss pattern on the body facing side of the film, a top surface film/air/synthetic menstrual fluid contact angle less than or equal to 70°, and a bottom contact angle less than or equal to 40°, with bottom contact angle less than or equal to top contact angle in an apertured film having micro-holes and large-sized holes in accordance with the invention (and which has the surfactant applied to the top female side and the film is rolled up to transfer surfactant to the male corona treated side), results in a film with limited fluid spreading in the non-apertured contiguous regions on the body facing side (see FIGS. 29 and 30), yet with a z-directional wettability differential or "hydrophilicity gradient", and excellent fluid wicking properties on the absorbent core side of the apertured film. These factors combine to deliver an absorbent article cover material that provides reduced leakage occurrence, and excellent fluid penetration and clean/dry properties. This cover may be especially useful in combination with other internal absorbent components designed to enhance horizontal wicking.

The example discussed immediately above offers a fluid penetration rate (as measured by 5 cc synthetic menstrual fluid strikethrough times—test method described in co-pending patent application Ser. No. 08/417,404), which is improved over non-surfactant-treated films by approximately 45%, in either a pulp absorbent core construction or a peat moss based absorbent construction.

The following Table 10 contains the results of a drop test measuring the time needed for absorption of one drop of synthetic menstrual fluid. In Table 10, the Cover refers to apertured film material. All of the covers contain micro-holes and large-sized holes. Covers 3 and 4 are made in accordance with the present invention, but differ with respect to the surface on which surfactant was initially applied. The test determines the time elapsed for the absorption of fluid, with a lower time being preferable and indicating greater absorption capacity.

TABLE 10

Effects Of Corona Orientation, Embossing And Surfactant Application On Cover Performance

| | | | Drop Test (sec) | |
|---|---|---|---|---|
| Cover # | Corona Position | Surfactant Application | Suspended Cover | Cover On Peat Moss Based Absorbent Core (no tilt) |
| 1 | top | top | >60 | >60 |
| 2 | top | bottom | >60 | >60 |
| 3 | bottom | top | 11 | 39 |
| 4 | bottom | bottom | 2 | 1 |
| 5 | top | none | >60 | >60 |
| 6 | bottom | none | >60 | >60 |

As seen from the reduced absorption times for covers 3 and 4, the above data confirms the advantages of applying surfactant to the bottom, corona treated surface of an apertured film topsheet.

What is claimed is:

1. A method for forming an apertured film from a stretchable thermoplastic polymeric material comprising:
   a) providing a starting film comprising said stretchable thermoplastic polymeric material and having a lower side that has been corona discharge treated and an upper side that has not been corona discharge treated;
   b) providing a backing member comprising localized support regions for supporting said starting film, recessed zones into which said starting film may be deformed by application thereto of fluids, and means for allowing said fluid to be transported away from said backing member;
   c) supporting said starting film on said backing member with portions of the lower side of said starting film being in contact with the support regions of said backing member and with the upper side of said starting film facing away from said backing member;
   d) forming irregular size micro-holes and large sized holes in said starting film by directing a fluid in the form of columnar streams from at least a first set and a second set of orifices against the upper side of said starting film in a zone of contact, the orifices of the first set each having a diameter greater than ten mils and the fluid supplied thereto having a pressure less than 500 psig. to cause said starting film to rupture into a multiplicity of said large sized holes in said starting film, the orifices of the second set each having a diameter less than or equal to ten mils and the fluid supplied thereto having a pressure of at least 500 psig. to cause the starting film to rupture into a multiplicity of said micro-holes in said starting film, whereby a combination of said large sized holes and said micro-holes are formed in said starting film to define an apertured film having a lower side and an upper side;
   e) moving said apertured film from said contact zone;
   f) applying a liquid coating of a surface active agent from an exterior source to the upper side of said apertured film which has not been corona discharge treated; and
   g) winding said apertured film into a roll with said lower side being in surface contact with said upper side, whereby at least a portion of said surface active agent is transferred from the upper side of the apertured film to the lower side thereof.

2. The method of claim 1 wherein said starting film is embossed to define a male side and a female side.

3. The method of claim 2 wherein the lower side of the starting film is the male side and the upper side of said starting film is the female side.

4. The method of claim 1 wherein said step (d) of directing a fluid includes directing said fluid from said first set of orifices against said starting film before directing said fluid from said second set of orifices against said starting film.

5. The method of claim 1 wherein the step of coating said apertured film is performed by applying the surface active agent in a water-based solution.

6. The method of claim 1 wherein the surface active agent is uniformly applied to the upper side of the apertured film.

7. A method of forming an apertured film having improved fluid distribution properties and comprising the steps of:
   a) providing an embossed starting film having a corona discharge treated male side and a female side that has not been corona discharge treated;
   b) supporting said embossed starting film on a three-dimensional forming member with the corona discharge treated male side of said film facing said forming member;
   c) directing a fluid in the form of columnar jets against the female side of said starting film with a force sufficient to form apertures in said starting film to define an apertured film having male and female sides corresponding to said starting film male and female sides;
   d) drying said apertured film;
   e) applying a liquid surface active agent from an exterior source to said apertured film female side which has not been corona discharge treated; and
   f) winding said apertured film into a roll with said male side being in surface contact with said female side, whereby at least a portion of said surface active agent is transferred from the female side of the apertured film to the male side thereof.

8. A method of forming an apertured film having improved fluid distribution properties and comprising the steps of:
   a) providing an embossed starting film having a male side and a female side;
   b) corona discharge treating the male side of said starting film but not the female side of said starting film;
   c) supporting said embossed starting film on a three-dimensional forming member with the corona discharge treated male side of said starting film facing said forming member and with the female side facing outwardly away from said forming member;
   d) directing a fluid in the form of columnar jets against the outwardly facing female side of said starting film with a force sufficient to form apertures in said starting film to define an apertured film having male and female sides corresponding to said starting film male and female sides;
   e) drying said apertured film;
   f) after step (e), applying a liquid surface active agent from an exterior source onto the exposed surface of one of said apertured film male and female sides; and
   g) winding said apertured film into a roll.

9. The method of claim 8 wherein said surface active agent is applied directly on the male side of said apertured film.

10. The method of claim 8 wherein said winding step includes transferring at least a portion of said surface active agent to the other of said apertured film male and female sides of said apertured film.

11. The method of claim 8 wherein said surface active agent is applied by coating the female side of said apertured film.

12. The method of claim 11, including transferring at least a portion of said surface active agent to the male side of said apertured film when said apertured film is wound into said roll.

13. The method of claim 12 wherein more than 50% of the surface active agent is transferred to the male side of the apertured film.

14. The method of claim 8 wherein said apertures include large sized holes.

15. The method of claim 8 wherein said surface active agent is applied to both of said apertured film male and female sides.

16. The method of claim 15 wherein greater than 50% of the applied surface active agent is distributed to said male side.

17. The method of claim 15 wherein greater than 75% of the applied surface active agent is distributed to said male side.

18. The method of claim 8 wherein said apertures include large sized holes and micro-holes.

19. The method of claim 8 wherein the step of coating said apertured film is performed by applying the surface active agent in a water-based solution.

20. The method of claim 8 wherein the surface active agent is uniformly applied to the corona discharge treated side of the apertured film.

21. A method for forming an apertured film from a stretchable thermoplastic polymeric material comprising the steps of:

a) providing a starting film comprising said stretchable thermoplastic polymeric material and having an upper side and a corona discharge treated lower side;

b) providing a backing member comprising localized support regions for supporting said starting film, recessed zones into which said starting film may be deformed by application thereto of fluids, and means for allowing said fluids to be transported away from said backing member;

c) supporting said starting film on said backing member with portions of the lower side of said starting film being in contact with the support regions of said backing member and with the upper side of said starting film facing away from said backing member;

d) forming irregular size micro-holes and large sized holes in said starting film by directing a fluid in the form of columnar streams from at least a first set and a second set of orifices against the upper side of said starting film in a zone of contact, the orifices of the first set having a diameter greater than ten mils and the fluid supplied thereto having a pressure less than 500 psig. to cause said starting film to rupture into a multiplicity of said large sized holes in said starting film, the orifices of the second set having a diameter less than or equal to ten mils and the fluid supplied thereto having a pressure of at least 500 psig. to cause the starting film to rupture into a multiplicity of said micro-holes in said starting film, whereby a combination of large sized holes and micro-holes are formed in said starting film to define an apertured film having lower and upper sides corresponding to said starting film lower and upper sides;

e) moving said apertured film from said contact zone and drying said apertured film; and f) after step (e), applying a liquid coating of a surface active agent from an exterior source onto the exposed surfaces of both of said apertured film upper and lower sides.

22. The method according to claim 21 wherein said step of applying a liquid coating of a surface active agent onto the exposed surfaces of both of said apertured film upper and lower sides comprises applying said coating of said surface active agent to one of the upper and lower sides of said apertured film to form an apertured film having a surface active agent coated side and an uncoated side, and winding said apertured film having said surface active agent coated side and said uncoated side into a roll with said surface active agent coated side being in surface-to-surface contact with said uncoated side, whereby at least a portion of said coating of said surface active agent is transferred from said surface active agent coated side to said uncoated side.

23. A method according to claim 22 wherein the corona discharge treated lower side is said surface active agent coated side.

24. A method according to claim 22 wherein the upper side of said apertured film is said surface active agent coated side.

25. A method according to claim 21 wherein said starting film is embossed to define a male side and a female side.

26. The method of claim 21 wherein the step of coating said apertured film is performed by applying the surface active agent in a water-based solution.

27. The method of claim 21 wherein the surface active agent is uniformly applied to the corona discharge treated lower side of the apertured film.

* * * * *